US009186321B2

(12) United States Patent
Bergstrom et al.

(10) Patent No.: US 9,186,321 B2
(45) Date of Patent: Nov. 17, 2015

(54) ORAL SPRAY FORMULATIONS AND METHODS FOR ADMINISTRATION OF SILDENAFIL

(71) Applicant: SUDA LIMITED, Osborne Park (AU)

(72) Inventors: David Bergstrom, Mendham, NJ (US); Foye Opawale, Flemington, NJ (US)

(73) Assignee: Suda Ltd., Osborne Park (AU)

( * ) Notice: Subject to any disclaimer, the term of this patent is extended or adjusted under 35 U.S.C. 154(b) by 0 days.

(21) Appl. No.: 14/363,245

(22) PCT Filed: Dec. 4, 2012

(86) PCT No.: PCT/US2012/067763
§ 371 (c)(1),
(2) Date: Jun. 5, 2014

(87) PCT Pub. No.: WO2013/085904
PCT Pub. Date: Jun. 13, 2013

(65) Prior Publication Data
US 2015/0051216 A1    Feb. 19, 2015

Related U.S. Application Data

(60) Provisional application No. 61/566,879, filed on Dec. 5, 2011.

(51) Int. Cl.
| | | |
|---|---|---|
| *A61K 31/519* | (2006.01) | |
| *A61K 9/00* | (2006.01) | |
| *A61K 47/10* | (2006.01) | |
| *A61K 9/08* | (2006.01) | |
| *A61K 47/02* | (2006.01) | |

(52) U.S. Cl.
CPC . *A61K 9/006* (2013.01); *A61K 9/08* (2013.01); *A61K 31/519* (2013.01); *A61K 47/02* (2013.01); *A61K 47/10* (2013.01)

(58) Field of Classification Search
CPC .................................................. A61K 31/519
See application file for complete search history.

(56) References Cited

U.S. PATENT DOCUMENTS

| | | | |
|---|---|---|---|
| 2005/0142069 A1 | 6/2005 | Dugger | |
| 2007/0031349 A1 | 2/2007 | Monteith et al. | |
| 2007/0042177 A1* | 2/2007 | Setsuda et al. ................. | 428/332 |
| 2009/0317461 A1* | 12/2009 | Bazemore et al. ............ | 424/464 |

FOREIGN PATENT DOCUMENTS

| | | | | |
|---|---|---|---|---|
| WO | WO-00/07597 A1 | 2/2000 | | |
| WO | WO 00/38655 | * 7/2000 | ............... | A61K 9/16 |
| WO | WO-01/35926 A2 | 5/2001 | | |
| WO | WO-2005/077374 A1 | 8/2005 | | |
| WO | WO-2007/002125 A1 | 1/2007 | | |
| WO | WO 2007/080382 | * 7/2007 | ........... | C07D 487/04 |

OTHER PUBLICATIONS

Wang Y, Chow MS, Zuo Z. Mechanistic analysis of pH-dependent solubility and trans-membrane permeability of amphoteric compounds: application to sildenafil. Int J Pharm. Mar. 20, 2008;352(1-2):217-24.*
Barnett et al., Sildenafil in the treatment of pulmonary hypertension. *Vasc. Health Risk Manag.* 2(4): 411-22 (2006).
Food and Drug Administration. Guidance for Industry: Bioavailability and Bioequivalence Studies for Orally Administered Drug Products—General Considerations. Center for Drug Evaluation and Research, Mar. 2003.
Handy, The Viagra® Craze, *Time*, 50-7 (May 4, 1998).
Huddleston et al., Sildenafil for the treatment of pulmonary hypertension in pediatric patients. *Ped. Patients*, 30(7): 871-82 (2009).
International Preliminary Report on Patentability, International Application No. PCT/US2012/067763, dated Jun. 10, 2014.
International Search Report and Written Opinion, corresponding International Application No. PCT/US2012/067763, mailed Feb. 15, 2013.
Luks et al., Medication and dosage considerations in the prophylaxis and treatment of high-altitude illiness. *Chest* 133: 744-55 (2008).
Mattar et al., Care of women in menopause: sexual function, dysfunction and therapeutic modalities. *Ann. Acad. Med. Singapore*, 37: 215-23 (2008).
Muirhead et al., Comparative human pharmacokinetics and metabolism of single-dose oral and intravenous sildenafil. *Br. J. Clin. Pharmacol.* 10(53): 13S-20S (2002).
Nichols et al., Pharmacokinetics of sildenafil after single oral doses in healthy male subjects: absolute bioavailability, food effects and dose proportionality. *Br. J. Clin. Pharmacol.* 53: 5S-12S (2002).
Shabsigh et al., Review of time of onset and duration of clinical efficacy of phosphodiesterase type 5 inhibitors in treatment of erectile dysfunction. *Urology*, 68(4): 689-96 (2006).
Sharma, Novel phophodiesterase-5 inhibitors: Current indications and future directions. *Indian J. Med. Sci.* 61: 667-79 (2007).
Stimmel, Sexual dysfunction and psychotropic medications. *CNS Spectr.* 11: 8 (Suppl 9): 24-30 (2006).
Uthayathas et al., Versatile effects of sildenafil: Recent pharmacological applications. *Pharmacological Reports* 59: 150-63 (2007).
Wang et al., Selective serotonin reuptake inhibitors in the treatment of premature ejaculation. *Chin. Med. J.* 120(11): 1000-6 (2007).

* cited by examiner

*Primary Examiner* — Paul Zarek
(74) *Attorney, Agent, or Firm* — Marshall, Gerstein & Borun LLP

(57) ABSTRACT

The present disclosure is directed to chemically-stable and pharmaceutically acceptable sildenafil oral spray formulations for the treatment of diseases such as pulmonary arterial hypertension and/or SSRI-induced sexual dysfunction, wherein the oral spray formulation has a pH of about 1.5 to less than 3.0. The present disclosure is also directed to methods for treating diseases such as pulmonary arterial hypertension and/or SSRI-induced sexual dysfunction.

19 Claims, 5 Drawing Sheets

Figure 7.2.6.1-1 Non-Dose-Adjusted Mean Plasma Sildenafil Concentration (0 – 24 hours) N = 24

Figure 7.2.6.3-1  Non-Dose-Adjusted Mean Plasma N-desmethylsildenafil Concentration (0 – 24 hours) N = 24

Figure 7.2.6.4-1  Dose-Adjusted Mean Plasma N-desmethylsildenafil Concentration (0 – 24 hours) N = 24

ORAL SPRAY FORMULATIONS AND METHODS FOR ADMINISTRATION OF SILDENAFIL

CROSS-REFERENCE TO RELATED APPLICATION

This application claims the benefit of priority of U.S. Provisional Application Ser. No. 61/566,879, filed Dec. 5, 2011. The foregoing application is incorporated herein by reference in its entirety.

FIELD OF THE INVENTION

This present disclosure relates to methods and formulations for delivery of sildenafil, and derivatives thereof, to the circulatory system by administration via an oral spray formulation to treat disease, such as pulmonary arterial hypertension and selective serotonin reuptake inhibitor (SSRI) induced sexual dysfunction.

BACKGROUND OF THE INVENTION

The U.S. Food and Drug Administration (FDA) has approved sildenafil citrate tablets for the treatment of pulmonary arterial hypertension (WHO Group I) under the brand name REVATIO®. The recommended dose of REVATIO® is 20 mg three times a day.

Sildenafil citrate was first approved by the FDA for the treatment of male erectile dysfunction under the brand name VIAGRA®.

Sildenafil is reported to be a selective inhibitor of cyclic-GMP-specific phosphodiesterase type 5 (PDE5). Its effects in treating pulmonary arterial hypertension (and erectile dysfunction) occur by enhancing the downstream effects of nitric oxide (NO) mediated vasorelaxation. PDE5 is found in pulmonary vascular smooth muscle and the corpus cavernosum, as well as in tissues such as vascular and visceral smooth muscle and in platelets. Sildenafil increases cyclic-GMP (cGMP) by inhibiting PDE5. PDE5 is responsible for degradation of cGMP. As a result, sildenafil increases cGMP within pulmonary vascular smooth muscle cells. In patients with pulmonary hypertension, this can lead to vasodilation of the pulmonary vascular bed and, to a lesser degree, vasodilation in the systemic circulation (see, e.g., REVATIO® product literature).

In addition to its therapeutic benefits in diseases such as pulmonary arterial hypertension (PAH) and erectile dysfunction, sildenafil is reported to be efficacious in the treatment of sexual dysfunctions associated with SSRI administration. See, e.g., Stimmel, G L, "Sexual dysfunction and psychotropic medications" CNS Spectr. (2006) 11:8(Suppl 9):24-30 and Wang, W-F et al. "Selective serotonin reuptake inhibitors in the treatment of premature ejaculation" Chin Med J (2007) 120(11):1000-1006. Sexual dysfunctions are a main side effect of SSRIs, and include difficulties with libido, arousal, delayed or absent orgasm (e.g., anorgasmia in women), and delayed ejaculation, anejaculation, or erectile dysfunction in men. Ibid. In patients suffering from sexual dysfunction as a result of SSRI treatment, administration of sildenafil as adjunct therapy may improve and sustain arousal, for example, in the patient by increasing blood flow, and sildenafil is thought to exert an indirect beneficial effect on other aspects of sexual response via the same mechanism. See, e.g., Stimmel, G L. CNS Spectr. (2006) 11:8(Suppl 9):24-30.

Sildenafil has been proposed as a possible therapeutic in the treatment of a number of other conditions as well. These include female sexual dysfunction, including sexual dysfunction associated with menopause, such as difficulties with sexual arousal. See, e.g., Mattar, C N et al. "Care of women in menopause: sexual function, dysfunction and therapeutic modalities" Ann Acad Med Singapore (2008) 37:215-223. Other conditions for which sildenafil may provide a therapeutic benefit include high-altitude illness (see, e.g., Luks, A M et al CHEST (2008) 133:744-755), pain, stroke, multiple sclerosis, and irritable bowel syndrome (see, e.g., Sharma, R Indian J Med Sci (2007) 61:667-679 and Uthayathas, S et al. Pharmacological Reports (2007) 59:150-163).

Despite its effectiveness in treating diseases such as PAH and erectile dysfunction, the administration of solid oral sildenafil dosage forms may also cause undesirable side effects. At high dosages, the incidence of such side effects increase, for example, abnormal vision problems (ranging from blue or green halo effects to blurring), dyspepsia, nasal congestion, blinding headaches, flushing, redness, diarrhea, dizziness, rash, and urinary tract infection. Other more serious side effects may occur in some cases resulting from a physiological predisposition, adverse drug interaction or potentiation, or by drug abuse. Such side effects include syncope (loss of consciousness), priapism (erection lasting 4 hours or more), and increased cardiac risk (coital coronaries). In particular, hypotension crisis may result from the combination of sildenafil citrate and organic nitrates, causing death in some cases. Hence, its administration to patients who are concurrently using organic nitrates (such as nitroglycerin) in any form is contraindicated. Moreover, the long-term effects of large doses of sildenafil-containing drugs are unknown (Handy B., "The Viagra® Craze," Time, pp. 50-57 (May 4, 1998)).

Many drugs exhibit low bioavailabilities owing to extensive first pass metabolism. Differences in bioavailability may have profound clinical significance. Sildenafil citrate, for example, exhibits only a 40% bioavailability after oral administration via tablet form, of which the active metabolite accounts for about one-half.

Compared to the administration of solid oral dosage forms absorbed in the gastrointestinal tract, the oral cavity presents the possibility for more rapid and efficient drug delivery because of its rich vascular supply. The oral cavity exhibits a minimal barrier to drug transport and may result in a rapid rise in serum concentration of drug.

However, the formulation of dosage forms for administration to the oral mucosa often poses non-trivial problems. For significant drug absorption to occur across the oral mucosa, the drug must have a prolonged exposure to the mucosal surface and the formulation must be both chemically stable and pharmaceutically acceptable to patients.

WO 01/35926 discloses sildenafil dosage forms for non-oral use, such as nasal delivery. However, there is currently no commercially available dosage form for oral spray delivery of sildenafil.

Thus, there is an ongoing need and desire for discreet and convenient sildenafil dosage forms for the treatment of diseases such as pulmonary arterial hypertension and SSRI-induced sexual dysfunction, which are both chemically stable and pharmaceutically acceptable.

SUMMARY OF THE INVENTION

The present disclosure is directed to methods and formulations for treating diseases such as pulmonary arterial hypertension and/or S SRI-induced sexual dysfunction. In particular, this disclosure relates to the oral administration of sildenafil or sildenafil citrate.

The disclosure herein is directed to an oral spray formulation for delivery of sildenafil to treat diseases such as pulmonary arterial hypertension and/or SSRI-induced sexual dysfunction. The sildenafil oral spray formulation may be a clear, colorless to light yellow, solution designed to be sprayed directly into the mouth, over or under the tongue.

In one aspect, the oral spray formulation may comprise sildenafil or a pharmaceutically acceptable salt thereof. In another aspect, the oral spray formulation may comprise sildenafil citrate.

In yet another aspect, the oral spray formulation comprising sildenafil or a pharmaceutically acceptable salt thereof may have a pH of about 1.5 to less than 3.0. In some embodiments, the pH of the formulation is about 2.2±0.5. In a certain embodiment, the pH of the formulation is about 2.2.

In still another aspect, the oral spray formulation may comprise a polar solvent. The polar solvent may comprise propylene glycol and ethyl alcohol. In certain embodiments, the ratio of propylene glycol:ethyl alcohol is about 62.5: 37.5% v/v.

In one aspect, said polar solvent may comprise one or more pH-adjusting agents. The pH-adjusting agents may be acidifying agents, alkalizing agents, or a combination thereof. In one aspect, the acidifying agent may be hydrochloric acid (HCl). In a particular embodiment, the HCl is present in an amount of about 10% v/v of the formulation. In another aspect, the alkalizing agent may be sodium hydroxide (NaOH). In a particular embodiment, the NaOH is present in an amount of about 2.1% v/v of the formulation.

In one aspect, the oral spray formulation comprising sildenafil or a pharmaceutically acceptable salt thereof may further comprise a taste-masking agent. In certain embodiments, the taste-masking agent comprises mint. In some embodiments, the mint is peppermint or spearmint. In other embodiments, the oral spray formulation further comprises a fruit and/or chocolate flavor. In some embodiments, the oral spray formulation comprises a sweetener. In a certain embodiment, the sweetener is sucralose.

In another aspect, the oral spray formulation may further comprise one or more pharmaceutically acceptable excipients, carriers, or a combination thereof.

The disclosure herein is also directed to a method for treating a disease such as PAH or SSRI-induced sexual dysfunction, which may comprise administering to a patient in need thereof a sildenafil oral spray formulation. In some embodiments, the sildenafil exposure in the patient results in a ln-transformed dose-adjusted to 25 mg geometric mean $AUC_{0-t}$ (ng-hr/mL) of approximately 299.36. In other embodiments, the sildenafil exposure in the patient results in a ln-transformed dose-adjusted to 25 mg geometric mean $AUC_{0-t}$ (ng-hr/mL) of approximately 323.16. In yet other embodiments, the sildenafil exposure in the patient results in a ln-transformed dose-adjusted to 25 mg geometric mean $AUC_{0-t}$ (ng-hr/mL) of approximately 304.98. In some embodiments, the sildenafil exposure in the patient results in a ln-transformed dose-adjusted to 25 mg geometric mean $AUC_{0-inf}$ (ng-hr/mL) of approximately 310.60. In other embodiments, the sildenafil exposure in the patient results in a ln-transformed dose-adjusted to 25 mg geometric mean $AUC_{0-inf}$ (ng-hr/mL) of approximately 331.22. In yet other embodiments, the sildenafil exposure in the patient results in a ln-transformed dose-adjusted to 25 mg geometric mean $AUC_{0-inf}$ (ng-hr/mL) of approximately 311.05.

In certain embodiments, the sildenafil is present in an oral spray formulation of the invention in an amount of about 7 to about 9% w/v of the formulation. In certain embodiments, it is present in an amount of about 8.31% w/v of the formulation. In other embodiments, the sildenafil salt is present in an amount of about 10 to about 12% w/v of the formulation. In a particular embodiment, the sildenafil salt is present in an amount of about 11.67% w/v of the formulation.

In some embodiments, the amount of sildenafil in an oral spray formulation of the invention that is administered per spray is 10 mg. In other embodiments, the amount of sildenafil administered per spray is 20 mg. In yet other embodiments, the amount of sildenafil administered per spray is 30 mg.

DETAILED DESCRIPTION

Figure 1:
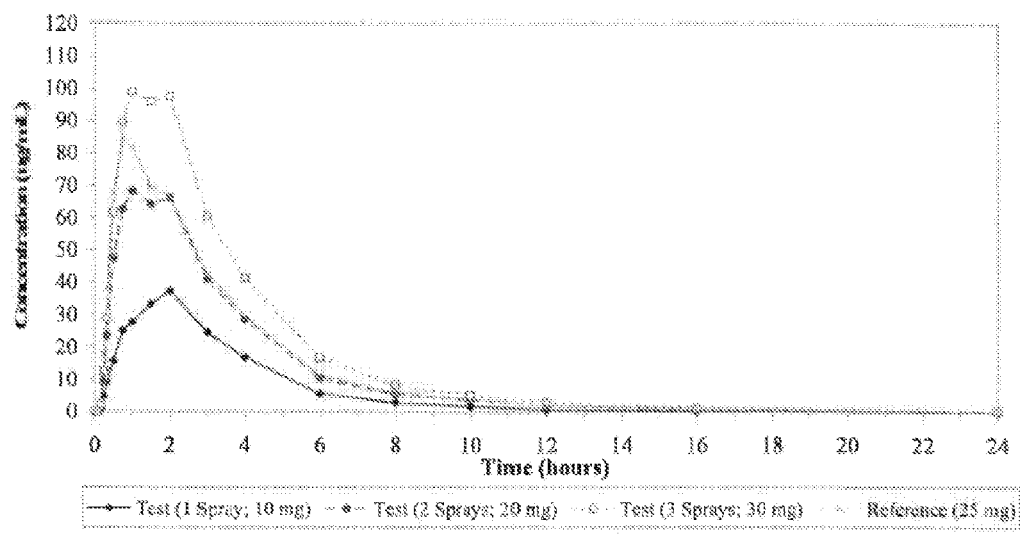
FIG. 1 (Figure 7.2.6-1-1) is a graph depicting non-dose-adjusted mean plasma sildenafil concentration (0-24 hours) N=24.
Figure 2:
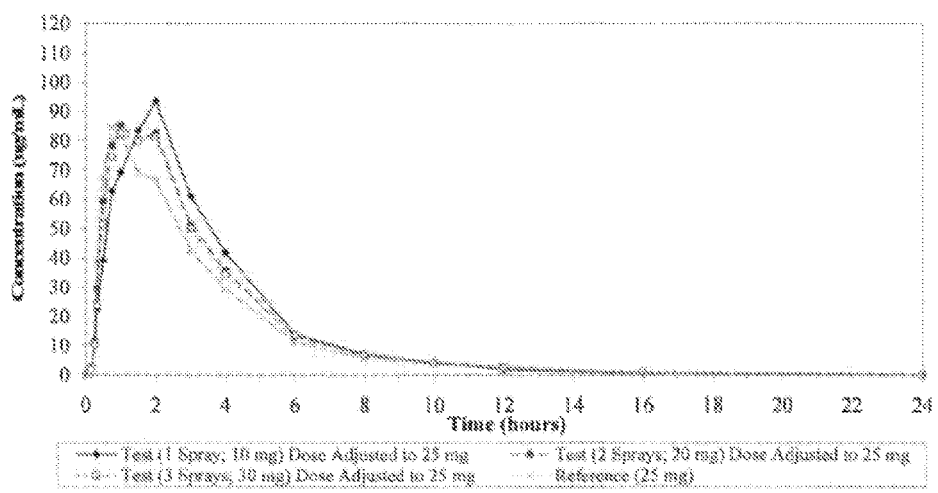
FIG. 2 (Figure 7.2.6.2-1) is a graph depicting dose-adjusted mean plasma sildenafil concentration (0-24 hours) N=24.
Figure 3:
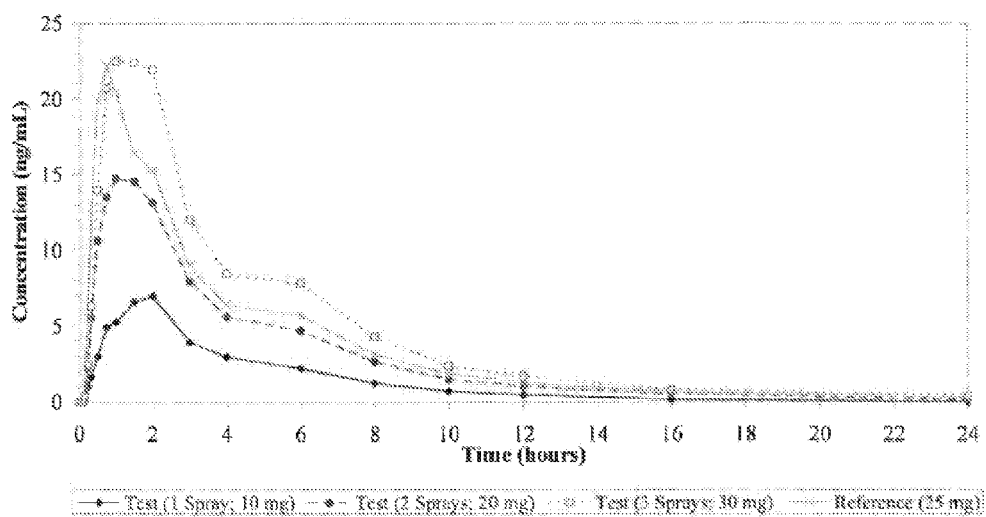
FIG. 3 (Figure 7.2.6.3-1) is a graph depicting non-dose-adjusted mean plasma N-desmethylsildenafil concentration (0-24 hours) N=24.
Figure 4:
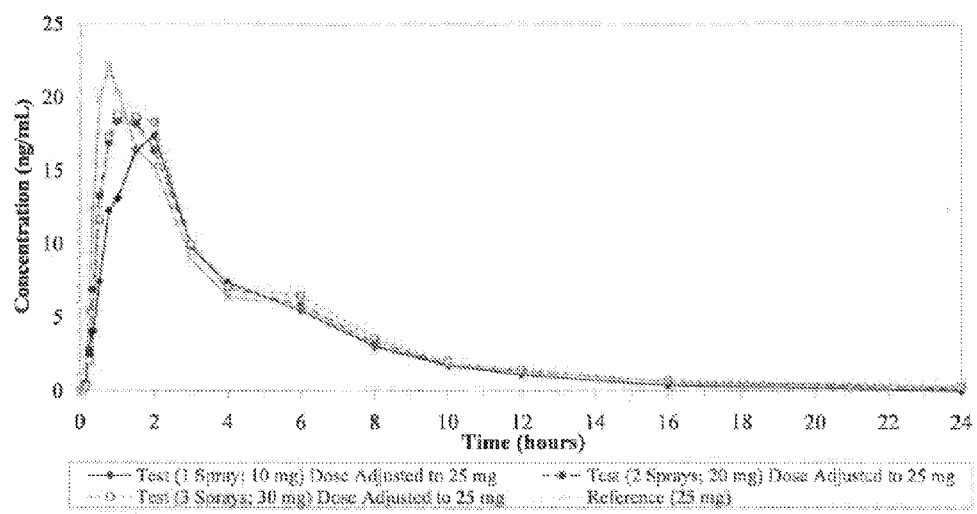
FIG. 4 (Figure 7.2.6.4-1) is a graph depicting dose-adjusted mean plasma N-desmethylsildenafil concentration (0-24 hours) N=24.
Figure 5:
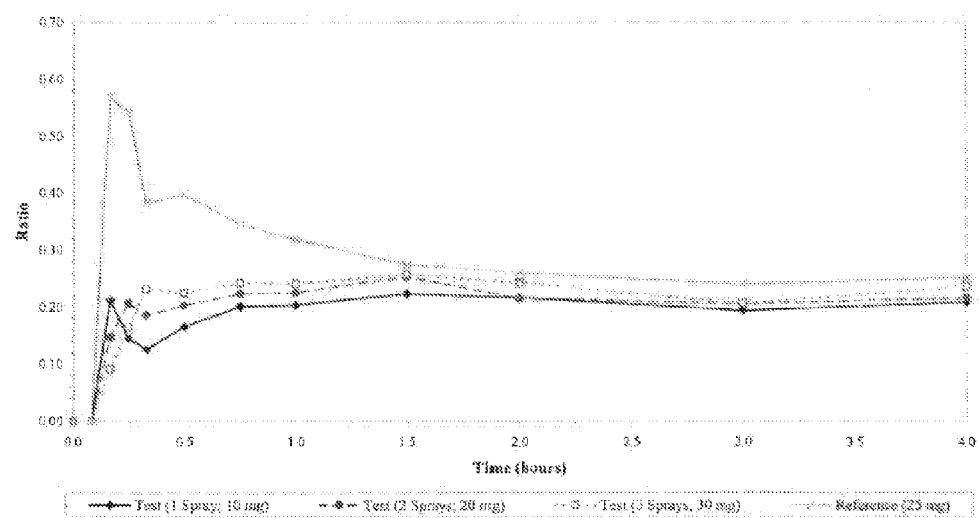
FIG. 5 (Figure 7.2.6.6-1) is a graph depicting mean plasma N-desmethylsildenafil/sildenafil ratio (0-4 hours) N=24.

Sildenafil is designated chemically as 1-[[3-(6,7-dihydro-1-methyl-7-oxo-3-propyl-1H-pyrazolo[4,3-d]pyrimidin-5-yl)-4-ethoxyphenyl]sulfonyl]-4-methylpiperazine.

The oral spray formulation disclosed herein comprises sildenafil or a pharmaceutically acceptable salt thereof. The term "pharmaceutically acceptable salts" refers to salts prepared from pharmaceutically acceptable non-toxic acids including organic and inorganic acids. Such acids include acetic, benzenesulfonic, benzoic, camphorsulfonic, citric, ethane-sulfonic, fumaric, gluconic, glutamic, hydrobromic, hydrochloric, isethionic, lactic, maleic, mandelic, methanesulfonic, mucic, nitric, pamoic, pantothenic, phosphoric, succinic, sulfuric, tartaric, and p-toluenesulfonic acids.

N-desmethylsildenafil is one known active metabolite of sildenafil.

Sildenafil, administered as the commercially available REVATIO® formulation for the treatment of pulmonary arterial hypertension (WHO Group I) to improve exercise ability and delay clinical worsening, is absorbed in the gastrointestinal tract after oral administration, with absolute bioavailability of about 40%. Based on the REVATIO® manufacturer's product literature, maximum observed plasma concentrations are reached within 30 to 120 minutes (median 60 minutes) of oral dosing in the fasted state. When the REVATIO® formulation is taken with a high-fat meal, the rate of absorption is reduced, with a mean delay in $T_{max}$ of 60 minutes and mean reduction in $C_{max}$ of 29%. The mean steady state volume of distribution (Vss) for sildenafil is reportedly 105 L, indicating distribution into the tissues.

The oral spray formulation disclosed herein is formulated for delivery via the oral cavity. The sildenafil oral spray formulation may be delivered transmucosally, sublingually, via the buccal cavity, via mucosal membranes and/or through the gastrointestinal tract.

The oral spray formulation of the instant application is suitable for use in the treatment of one or more diseases for which sildenafil administration is considered efficacious. Examples of such diseases include PAH, SSRI-induced sexual dysfunction, and erectile dysfunction. In certain embodiments, a sildenafil oral spray formulation of the instant application is suitable for use in the treatment of HIV-associated PAH; hemolysis associated PAH; portopulmonary hypertension; PAH in pediatric patients (e.g., idiopathic PAH, post op congenital heart defect repair, and Eisenmenger syndrome); pulmonary hypertension associated with heart failure, cardiac surgery, and cardiac transplant; pulmonary thromboembolic disease; pulmonary fibrosis associated pulmonary hypertension; and/or altitude-associated pulmonary hypertension. See, e.g., Barnett, C F et al. Vascular Health and Risk Management (2006) 2(4):411-422. In other embodiments, a sildenafil oral spray formulation of the instant application is suitable for use in the treatment of female sexual dysfunction, including sexual dysfunction associated with menopause, such as difficulties with sexual arousal. In yet other embodiments, a sildenafil oral spray formulation of the instant application is suitable for use in the treatment of high-altitude illness, pain, stroke, multiple sclerosis, and/or irritable bowl syndrome.

The oral spray formulation as disclosed may comprise sildenafil base or a pharmaceutically acceptable salt thereof in an amount of about 6 to about 14% w/v, about 7 to about 13% w/v, or about 8 to about 12% w/v of the formulation. In one aspect, the oral spray formulation may comprise sildenafil or a pharmaceutically acceptable salt thereof in an amount of about 8 to about 10% w/v of the formulation.

In another aspect, the oral spray formulation as disclosed may comprise sildenafil base in an amount of about 6 to about 10% w/v, about 7 to about 9% w/v, or about 8% w/v of the formulation. In yet another aspect, the oral spray formulation may comprise sildenafil base in an amount of about 8.31% w/v of the formulation.

In one aspect, the oral spray formulation as disclosed may comprise sildenafil citrate in an amount of about 10 to about 14% w/v, about 11 to about 13% w/v, or about 12% w/v of the formulation. In another aspect, the oral spray formulation may comprise sildenafil citrate in an amount of about 11.67% w/v of the formulation.

The oral spray formulation as disclosed may deliver sildenafil base or a pharmaceutically acceptable salt thereof in an amount (per spray) of about 3 to about 25 mg, about 6 to about 20 mg, about 8 to about 18 mg, about 10 to about 16 mg, or about 12 to about 14 mg.

In one aspect, the oral spray formulation may deliver sildenafil base in an amount (per spray) of about 6 to about 14 mg, or about 8 to about 12 mg. In another aspect, the oral spray formulation may deliver about 10 mg per spray.

In yet another aspect, the oral spray formulation may deliver sildenafil citrate in an amount (per spray) of about 10 to about 18 mg, or about 12 to about 16 mg. In still another aspect, the oral spray formulation may deliver about 14 mg per spray.

In one aspect, one to five sprays of the oral spray formulation may be administered to a patient. In another aspect, one to three sprays of the sildenafil formulation are delivered to a patient. In yet another aspect, the spray may deliver about 100 to about 120 µl (about 0.1 to about 0.12 mL) of the formulation. In still another aspect, the spray may deliver about 120 µl of the formulation. In some embodiments, the spray delivers about 200 to about 250 µl of the formulation. In certain embodiments, the spray delivers about 250 µl of the formulation.

The oral spray formulation as disclosed may have a pH of about 1.5 to less than 3.0. In one aspect, the pH of the oral spray formulation may be 1.5, 1.6, 1.7, 1.8, 1.9, 2.0, 2.1, 2.2, 2.3, 2.4, 2.5, 2.6, 2.7, 2.8, or 2.9. In another aspect, the pH of the oral spray formulation of the may be about 2.210.5, or about 2.310.5.

Polar solvents of the disclosed oral spray formulation may include, but are not limited to, ethyl alcohol, propylene glycol, glycerol and polyethylene glycols having a nominal molecular weight of 200-600 g/mol, N-methyl-2-pyrrolidone, or combinations thereof. In one aspect, the polar solvent may comprise propylene glycol and dehydrated alcohol (e.g., ethyl alcohol). Propylene glycol and dehydrated alcohol may be comprised within the oral spray formulation at a propylene glycol:alcohol ratio of about 70:30% v/v, about 65:35% v/v, about 60:40% v/v, about 55:45% v/v, or about 50:50% v/v. In another aspect, the propylene glycol:alcohol ratio may be about 62.5:37.5% v/v.

In one aspect, propylene glycol is present in an amount of about 55% v/v and ethyl alcohol is present in an amount of about 33% v/v of the final oral spray formulation.

Formulations as disclosed may comprise one or more pH-adjusting agents. pH-adjusting agents may include acidifying agents or alkalizing agents. Acidifying agents of the present invention may include, but are not limited to, hydrochloric acid, citric acid, lactic acid, glycolic acid, acetic acid, glacial acetic acid, malic acid, and proprionic acid. Alkalizing agents of the present invention may include, but are not limited to, sodium hydroxide, edetol, potassium carbonate, potassium hydroxide, sodium borate, sodium carbonate, sodium citrate, sodium lactate, and sodium glycolate. In one aspect, the oral spray formulation may comprise an acidifying agent, an alkalizing agent, or a combination thereof. The acidifying agent may be present in the solvent in an amount of about 5 to about 15% v/v of the solvent, or about 10% v/v of the solvent. The alkalizing agent may be present in the solvent in an amount of about 1.5 to about 4% v/v of the solvent, or about 2.1% v/v of the solvent.

The $C_{max}$ obtained after administration of the disclosed oral spray formulation may be, but is not limited to, about 50 to about 150% of a reference $C_{max}$. In one aspect, the reference $C_{max}$ may be the $C_{max}$ obtained following administration of sildenafil citrate tablets. In another aspect, the $C_{max}$ obtained after administration of the disclosed oral spray formulation may meet bioequivalence standards, as set forth by the FDA, including that the 90% confidence interval of the geometric mean ratio of $C_{max}$ between the test and reference product fall within 80-125%.

The AUC obtained after administration of the disclosed oral spray formulation may be, but is not limited to, about 50 to about 150% of a reference AUC. In one aspect, the reference AUC may be the AUC obtained following administration of sildenafil citrate tablets. In another aspect, the AUC obtained after administration of the disclosed oral spray formulation may meet bioequivalence standards, as set forth by the FDA, including that the 90% confidence interval of the geometric mean ratio of AUC between the test and reference product fall within 80-125%.

The $T_{max}$ obtained after administration of the disclosed oral spray formulation may be, but is not limited to, about 50 to about 150% of a reference $T_{max}$. In one aspect, the reference $T_{max}$ may be the $T_{max}$ obtained following administration of sildenafil citrate tablets. In another aspect, the $T_{max}$ obtained after administration of the disclosed oral spray formulation may meet bioequivalence standards, as set forth by the FDA, including that the 90% confidence interval of the geometric mean ratio of $T_{max}$ between the test and reference product fall within 80-125%. The oral spray formulation as disclosed may further comprise one or more pharmaceutically acceptable excipients, carriers, or a combination thereof.

Excipients may include, but are not limited to, co-solvents and/or solubilizing agents, penetration enhancers, stabilizing agents, buffering agents, tonicity agents, anti-microbial agent, and viscosity-modifying agents.

Co-solvents may include, but are not limited to, ethyl alcohol, propylene glycol, glycerol and polyethylene glycols having a nominal molecular weight of 200-600 g/mol, and N-methyl-2-pyrrolidone.

Solubilizing agents may include, but are not limited to, purified diethylene glycol monoethyl ether, cyclodextrins, glycerol monostearate, lecithin, poloxomer, polyethylene alkyl ethers, polyoxyethylene castor oil derivatives, polyoxyethylene sorbitan fatty acid esters, polyoxyethylene stearates, stearic acid, citric acid, and ascorbic acid and the like; surface active agents such as polysorbates, sorbiton esters, polyvinyl alcohol, benzal konium chloride, benzithonium chloride, cetrimide, docusate sodium, sodium lauryl sulphate, and octoxynol.

Solubility enhancers may include, but are not limited to, DL-methionine, caffeine, nicotinamide, vanillin, benzyl alcohol, ethanol, and Transcutol (diethylene glycol monoethyl ether). In certain embodiments, a formulation of the invention comprises caffeine as a solubility enhancer. In further embodiments, caffeine is present in the formulation in an amount of about 25 mg/mL. In certain embodiments, a formulation of the invention comprises nicotinamide as a solubility enhancer. In further embodiments, nicotinamide is present in the formulation in an amount of about 5% w/w.

Buffering agents may include, but are not limited to, hydrochloric acid, sodium acetate, glacial acetic acid, orthophosphoric acid, and potassium dihydrogen orthophosphate.

Stabilizing agents may include, but are not limited to, sodium metabisulphite, sodium bisulphite, disodium EDTA, and ascorbic acid.

Anti-microbial agents may include, but are not limited to, benzyl alcohol, benzalkonium chloride, phenyl mercuric acetate, and phenylethyl alcohol.

Viscosity-modifying agents may include, but are not limited to, hydroxypropyl methylcellulose, and poly acrylic acid, or water soluble polymers such as carbopol, sodium carboxymethyl cellulose, hydroxypropyl cellulose, hydroxyethyl cellulose and various grades of polyvinylpyrrolidone (e.g., K-15, K-30, K-60, and K-90).

In certain embodiments, it may be desirable to increase the mucosal (e.g., oral mucosal) residence time of sildenafil that is administered to a patient in an oral spray formulation as disclosed herein. Accordingly, in certain embodiments, an oral spray formulation of the instant application may comprise one or more permeation enhancers and/or mucoadhesives. Examples of suitable permeation enhancers include nicotinamide, caffeine, peppermint oil, sodium glycocholate, phospholipids, alkyl saccharides, aprotinin, benzalkonium chloride, ceramides, cetylpyridinium chloride, chitosan, chitosan-4-thiobutylamidine, cyclodextrins, dextran sulfate, dodecyl azacycloheptyl-2-ketone, ether lipids (plasmologens), glycerol, glycosylated sphingosines, lauric acid, 23-lauryl ether, lysophosphatidylcholine, menthol, methoxysalicylate, phosphatidyl choline, 1-palmitoyl-2-glutaroyl-sn-glycero-3-phosphocholine, polycarbophil cysteine, poly-L-arginine, polyoxyethylene, polyoxyethylene-9-lauryl ether, polysorbate 80, propylene glycol, EDTA, sodium deoxycholate, sodium glycocholate, sodium glycodeoxycholate, sodium lauryl sulfate, sodium salicylate, sodium taurocholate, sodium taurodeoxycholate, sodium taurodihydrofusidate, sphingolipids, and sterols. Examples of suitable mucoadhesives include hydroxypropyl cellulose, gelatin, crosslinked polyacrylic acid, polymethacrylic acid, polyhydroxyethyl methacrylic acid, hydroxypropyl methyl cellulose, polyethylene glycol, sodium carboxymethyl cellulose, hyaluronic acid, chitosan, polycarbophil, pectin, xanthan gum, alginate, copolymers of dextran, polyacrylamide, acacia, copolymer of caprolactone and ethylene oxide, carbopol 934, tragacanth, and eudragit.

The oral spray formulation as disclosed may comprise taste-masking or flavoring agents. Taste-masking or flavoring agents as used herein are agents that may hide or minimize an undesirable flavor such as a bitter or sour flavor. Examples of taste-masking or flavoring agents suitable for use in the formulations of the present invention include, but are not limited to, synthetic or natural peppermint oil, spearmint oil, citrus oil, fruit flavors (e.g., citrus, such as orange, lemon, lime; strawberry; cherry; grape; melon; and mixtures thereof), chocolate, spice (e.g., anise, cinnamon), vanilla, bubblegum, and sweeteners (e.g., sugars, aspartame, saccharin, and sucralose). In certain embodiments, the oral spray formulation comprises a sweetener that is sucralose. In certain embodiments, the taste-masking or flavoring agent is mint. In certain embodiments, the mint is peppermint. In further embodiments, the mint is a strong mint, e.g., peppermint oil NF. In yet other embodiments, a formulation of the invention comprises a taste-masking or flavoring agent that is chocolate mint.

Taste-masking and/or flavoring agents may be evaluated in a formulation of the invention according to the Flavor Profile Method (see Keane, P. The Flavor Profile Method. In C. Hootman (Ed.), Manual on Descriptive Analysis Testing for Sensory Evaluation ASTM Manual Series: MNL 13. Baltimore, Md. (1992)), for example, to identify, characterize, and/or quantify sensory attributes of products, e.g., basic tastes, aroma, texture, and mouthfeel.

In certain embodiments, a formulation of the invention comprises a taste-masking and/or flavoring agent that achieves an intensity similar to that of a common breath mint spray. In some embodiments, the buffer strength of the formulation is reduced (e.g., through a reduction in NaOH levels) to achieve a desired balance in formulation taste (e.g., balanced basic tastes).

The oral spray formulation as disclosed may be packaged in amber Type 1 glass Schott bottles configured with 100 or 120 µl snap-on Pfeiffer pumps, or within any type of pharmaceutically-acceptable package, container, pump, or bottle.

In one aspect, the oral spray formulation as disclosed consists of sildenafil citrate, propylene glycol, ethyl alcohol, hydrochloric acid, and sodium hydroxide.

In another aspect, the oral spray formulation consists of sildenafil citrate, propylene glycol, ethyl alcohol, hydrochloric acid, sodium hydroxide, and a taste-masking agent.

In yet another aspect, the oral spray formulation consists essentially of sildenafil citrate, propylene glycol, ethyl alcohol, hydrochloric acid, and sodium hydroxide.

In still another aspect, the oral spray formulation consists essentially of sildenafil citrate, propylene glycol, ethyl alcohol, hydrochloric acid, sodium hydroxide, and a taste-masking agent.

The following non-limiting examples will further describe the disclosed oral spray formulation.

Example 1

The commercially available, citrate salt form of sildenafil was selected as the active pharmaceutical ingredient in the development of an oral spray form.

The final solvent system included a combination of 62.5% v/v propylene glycol to 37.5% v/v alcohol mixture acidified with 0.5 mL dilute HCl and pH adjusted to 2.0 or less using 5N NaOH. This combination was able to solubilize 12 to 14% w/v sildenafil citrate and keep the API in solution.

TABLE

Composition of the formulation vehicle designed to deliver 14 mg citrate salt (10 mg base equivalent) per 0.12 mL spray

| Ingredient | Concentration | Target amounts in 250 mL |
|---|---|---|
| Sildenafil citrate | 11.67% w/v | 29.175 g |
| Propylene glycol/ethanol Mixture 62.5%/37.5% v/v or 68.4%/31.6% w/w | ~70% v/v | 175 mL |
| Diluted HCL (10% v/v) | 10% v/v | 25 mL |
| 5N NaOH | 2.1% v/v | 5.25 mL |
| Propylene glycol/ethanol mixture | Qs | 250 mL |

The sildenafil citrate solution (having a salt concentration of 11.67% w/v (11.67 mg/mL)) may be administered to a patient in a commercially available pump spray designed to deliver 14 mg salt/120 µl of spray (or 10 mg base/120 µl of spray).

The formulation vehicle was stable when stored 25° C./60% RH and 40° C./75% RH for six months.

Example 2

Subjects are provided sildenafil citrate in an oral spray dosage form as a part of a single-dose study. One subset of subjects is administered one spray of an oral spray sildenafil formulation comprising 14 mg sildenafil citrate per spray (providing a total administered amount equivalent to 10 mg sildenafil base). A second subset of subjects is administered two sprays of an oral spray sildenafil formulation comprising 14 mg sildenafil citrate per spray (providing a total administered amount equivalent to 20 mg sildenafil base). A third subset of subjects is administered three sprays of an oral spray sildenafil formulation comprising 14 mg sildenafil citrate per spray (providing a total administered amount equivalent to 30 mg sildenafil base).

Example 3

A Relative Bioavailability Study of Sildenafil Oral Spray at 10 mg, 20 mg, and 30 mg Doses Versus 25 mg VIAGRA® Tablets Under Fasting Conditions Objective This study assessed the relative bioavailability of sildenafil oral spray compared to that of VIAGRA® tablets by Pfizer Labs following a single oral dose [1×14 mg/0.12 mL sildenafil citrate oral spray (equivalent to 10 mg sildenafil base), 2×14 mg/0.12 mL sildenafil citrate oral sprays (equivalent to 20 mg sildenafil base), 3×14 mg/0.12 mL sildenafil citrate oral sprays (equivalent to 30 mg sildenafil base), or 1×25 mg tablet] in healthy adult subjects when administered under fasting conditions.

Secondary objectives were to assess the relative safety of the sildenafil oral spray following single oral dose administration compared to that of VIAGRA® tablets. Assessments include evaluation of changes in orthostatic hypotension, oral irritation, vital sign assessments, 12-lead electrocardiogram (ECG), and clinical assessments.

Study Design

This was an open-label, single-dose, randomized, four-period, four-treatment crossover study under fasting conditions. The total number of healthy adult male subjects enrolled in the study was twenty-four (24). The total duration of the study, screening through study exit, was approximately nine weeks with at least a three-day washout period between doses. At study check-in, the subjects reported to the clinical site at least 36 hours prior to Day 1 dosing for Period I and at least 12 hours prior to Day 1 dosing for Periods II, III, and IV. Subjects were required to stay for at least 24 hours after each treatment period.

Following each washout period, subjects returned to the clinical facility to be dosed with the alternative treatments as per the randomization. Blood sample collection was obtained within 90 minutes, but no later than 30 minutes, prior to dosing (0 hour) and after dose administration at 0.083, 0.167, 0.25, 0.33, 0.50, 0.75, 1, 1.5, 2, 3, 4, 6, 8, 10, 12, 16, and 24 hours. The actual time of sample collection was documented. During each study period, a total of 18 blood samples were collected for a total of 72 samples and 432 mL total volume. The actual time of sample collection was documented.

Bioanalytical Sample Analyses

The sildenafil and N-desmethylsildenafil plasma concentrations were measured using a validated bioanalytical method and according to the standard operating procedures and FDA Guidelines. The validated detection range for sildenafil is 1 to 300 ng/mL in human plasma. The validated detection range for N-desmethylsildenafil is 0.25 to 75 ng/mL in human plasma.

Pharmacokinetic Data Analyses

Pharmacokinetic parameters for plasma sildenafil and N-desmethylsildenafil concentration were calculated using standard noncompartmental approaches as indicated below:

$AUC_{0-t}$ The area under the plasma concentration versus time curve, from time 0 to the last measurable concentration, as calculated by the linear trapezoidal method.

$AUC_{0-inf}$ The area under the plasma concentration versus time curve from time 0 to infinity. $AUC_{0-inf}$ is calculated as the sum of the $AUC_{0-t}$ plus the ratio of the last measurable plasma concentration to the elimination rate constant.

$AUC_{0-t}/AUC_{0-inf}$ The ratio of $AUC_{0-t}$ to $AUC_{0-inf}$.

$C_{max}$ Maximum measured plasma concentration over the time span specified.

$T_{max}$ Time of the maximum measured plasma concentration. If the maximum value occurs at more than one time point, $T_{max}$ is defined as the first time point with this value.

Kel Apparent first-order terminal elimination rate constant calculated from a semi-log plot of the plasma concentration versus time curve. The parameter will be calculated by linear least-squares regression analysis in the terminal log-linear phase (three or more non-zero plasma concentrations).

$T_{1/2}$ The apparent first-order terminal elimination half-life will be calculated as 0.693/Kel.

Ratio The ratio of metabolite/parent will be assessed at each concentration as well for Metabolite/Parent PK parameters $C_{max}$, $AUC_{0-t}$, and $AUC_{0-inf}$.

No value of Kel, $AUC_{0-inf}$, or $T_{1/2}$ will be reported for cases that do not exhibit a terminal log-linear phase in the concentration versus time profile. Other pharmacokinetic parameters may be calculated if deemed necessary.

Statistical Analyses

Arithmetic means, standard deviations and coefficients of variation were calculated for the parameters listed above. Additionally, geometric means were calculated for $AUC_{0-t}$, $AUC_{0-inf}$ and $C_{max}$.

Analyses of variance (ANOVA) were performed on the ln-transformed pharmacokinetic parameters $AUC_{0-t}$, $AUC_{0-inf}$ and $C_{max}$. The ANOVA model includes sequence, formulation and period as fixed effects and subject nested within sequence as a random effect. Sequence is tested using subject nested within sequence as the error term. A 10% level of significance is used to test the sequence effect. Each analysis of variance includes calculation of least-squares means, the difference between adjusted formulation means and the standard error associated with this difference. The above statistical analyses were performed using the appropriate SAS® procedure.

In agreement with the two one-sided test for bioequivalence, 90% confidence intervals for the difference between drug formulation least-squares means (LSM) were calculated for the parameters $AUC_{0-t}$, $AUC_{0-inf}$ and $C_{max}$ using ln-transformed data. The confidence intervals are expressed as a percentage relative to the LSM of the reference formulation.

Ratios of means were calculated using the LSM for ln-transformed $AUC_{0-t}$, $ACU_{0-inf}$ and $C_{max}$. The geometric mean values are reported. Ratios of means are expressed as a percentage of the LSM for the reference formulation.

Bioequivalence is based on the 90% confidence intervals for sildenafil.

Mouth Preparation

Between 1.25 hours (study hour −1.25) and 1 hour (study hour −1) prior to dosing, including Period I Day −1 placebo dose, subjects brushed their teeth and tongue with toothpaste provided by the clinical site. After completing the brushing, subjects immediately rinsed their mouths three times with approximately 80 mL of room temperature water to total 240 mL (8 fluid ounces).

Saliva pH Assessments

Saliva pH was measured at 2300 hours (±30 minutes) on Day −1, and on Day 1 within 30 minutes prior to teeth and tongue brushing, within 30 minutes of completion of teeth and tongue brushing, and within 15 minutes prior to dosing. For the placebo dose (Day −1 of Period I), the saliva pH was measured at 2300 hours (+30 minutes) on Day −2, and on Day −1 within 30 minutes prior to teeth and tongue brushing, within 30 minutes of completion of teeth and tongue brushing, and within 15 minutes prior to placebo dosing. The pH was measured using pH test strips with a range of 5-9. Any subject that had a pH of 5 was additionally tested with pH test strips with a range of 0-6.

Oral Spray Administration

Within 30 minutes prior to administration, the spray product bottle was primed by actuating five sprays according to priming instructions provided by the sponsor prior to study start. A new spray bottle was used for each subject for each dose.

At the time of dosing, subjects were instructed to open their mouths and place their relaxed tongues against their bottom rows of teeth. Study staff then administered the appropriate number of sprays according to the randomization schedule.

After dosing, subjects were instructed to close their mouths and place their tongues against their bottom row of teeth for two minutes. Subjects were instructed not to swallow or swish around the product in their mouth during the two minutes. After two minutes, the subjects were instructed to swallow and any deviation from this time was recorded. After swallowing was complete, an objective oral irritation assessment (soft tissue irritation within the labial or buccal mucosa and tongue) was performed.

Reference Product Administration

A single 25 mg dose of Viagra® Tablets (1×25 mg) was administered on Day 1 dosing with approximately 240 mL (8 fluid ounces) of room temperature water. Site personnel ensured the entire dose and fluid were swallowed.

Post-Dose Questionnaire

Immediately after dosing was completed and at one hour after dosing, subjects were queried on the following regarding the test product:

Taste of the product

Willingness to take the product again

Any presence of excessive salivation

If oral irritation persisted beyond one hour, subjects were queried at all irritation evaluations after one hour with the following: "How does your mouth feel?"

Study Procedures

Study Check-In (Day −2 of Period I)

At study check-in, the subjects reported to the clinical site at least 36 hours prior to Day 1 dosing and were required to stay for 24 hours after Day 1 dosing. The subjects were evaluated to assess if they continued to meet the study inclusion/exclusion and restriction criteria. Water was allowed ad libitum during fasting. Supine and standing blood pressure and heart rate, and an electrocardiogram were collected. A urine sample was collected for a drug abuse screen.

Subjects began fasting at least ten hours prior to dosing on Day −1. Throughout the study, standardized meals and beverages were served. Meals were the same in content and quantity during each confinement period. At 2300 hours (±30 minutes), saliva pH was measured prior to nighttime teeth brushing. Subjects were instructed to go to bed after completing this assessment.

On Day −1 of Period I only, subjects received three sprays of the placebo test product at 24 hours prior to Period I Day 1 dosing. Dose preparation and administration were identical to the test product procedures.

Study Check-In (Day −1 of Periods II, III, & IV)

At study check-in, the subjects reported to the clinical site at least 12 hours prior to Day 1 dosing and were required to stay for 24 hours after Day 1 dosing. The subjects were briefly evaluated to assess if they continued to meet the study inclusion/exclusion and restriction criteria. Water was allowed ad libitum during fasting. Supine and standing blood pressure and heart rate, and an electrocardiogram were collected. A urine sample was collected for a drug abuse screen. Subjects began fasting at least ten hours prior to dosing on Day 1. Throughout the study, standardized meals and beverages were served. Meals were the same in content and quantity during each confinement period. At 2300 hours (±30 minutes), saliva pH was measured prior to nighttime teeth brushing. Subjects were instructed to go to bed after completing this assessment.

Study Day Procedures (Day −1 of Period I)

Prior to placebo dosing, the following activities were completed:

Measured saliva pH before subject brushed their teeth and the tongue

Subjects brushed their teeth and tongue prior to dose administration

Measured saliva pH after subject brushed their teeth and tongue

Measured saliva pH within 15 minutes prior to dose administration

Assessed the oral cavity for baseline oral irritation prior to placebo administration No fluid was allowed from one hour prior to dose administration until one hour after dosing.

At 24 hours prior to Day 1 dosing, each subject was dosed sequentially with one dose (three sprays) of placebo oral spray during Period I for a total of one dose per subject.

After placebo dosing, the following activities were completed:

Both objective and subjective oral irritation assessments were performed immediately after dosing and at one hour after placebo dose administration.

A fast was maintained until at least four hours after placebo dosing. During the study confinement period, fluid consumption resumed at no sooner than one hour after dose administration. When fluids are not restricted, they were allowed ad libitum.

Subjects were not allowed to brush their teeth and tongue for the first two hours after dosing.

Lunch was provided at study hour 4.25 after placebo dose administration.

Dinner was provided at study hour 10.25 after placebo dose administration.

An evening snack was provided at 10.5 hours prior to dose administration on Day 1.

At 2300 hours (±30 minutes), saliva pH was measured prior to nighttime teeth and tongue brushing. Subjects were instructed to go to bed after completing this assessment.

Subjects began fasting at least ten hours prior to dosing on Day 1.

Day 1

Prior to dosing, the following activities were completed:

Collected supine and standing blood pressure and heart rate.

Measured saliva pH before subject brushed their teeth and the tongue.

Subjects brushed their teeth and tongue prior to dose administration.

Measured saliva pH after subject brushed their teeth and tongue.

Collected a pre-dose 0 hour blood sample for pharmacokinetic analysis.

Measured saliva pH within 15 minutes prior to dose administration.

Assessed the oral cavity for baseline oral irritation.

No fluid, except that given with reference drug administration, was allowed from one hour prior to dose administration until one hour after dosing.

Each subject was dosed sequentially with one dose (1×14 mg/0.12 mL oral spray, 2×14 mg/0.12 mL oral spray, 3×14 mg/0.12 mL oral spray, or 1×25 mg tablet) in each of the four dosing periods for a total of four doses per subject.

After dosing, the following activities were completed:

Both objective and subjective oral irritation assessments were performed immediately after dosing and at one hour after dose administration.

A fast was maintained until at least four hours after dosing. During the study confinement period, fluid consumption resumed no sooner than one hour after dose administration. When fluids were not restricted, they were allowed ad libitum.

Subjects were not allowed to brush their teeth and tongue for the first two hours after dosing.

Subjects were closely supervised and within sight of study personnel for four hours after receiving their initial dose.

The subjects remained seated upright for the first four hours after dosing, except as otherwise required for study procedures or personal needs. Subjects were not allowed to lie down (except as directed by Clinical staff secondary to adverse events) for the first four hours after dosing. Subjects did not engage in any strenuous activity while confined to the clinic and followed the rules governing their activities as set forth by the clinic.

Lunch was provided at study hour 4.25.

Dinner was provided at study hour 10.25

An evening snack was provided at study hour 14.25.

Blood sample collections were obtained as per the profile.

Supine and standing blood pressure and heart rate were measured at approximately one hour after each dose.

An electrocardiogram was measured at approximately one hour after each dose.

All subjects were evaluated for the presence of any adverse events.

Day 2

Blood sample collections were obtained as per the profile.

Supine and standing blood pressure and heart rate was measured at approximately 24 hours after each dose.

All subjects were evaluated for the presence of any adverse events prior to release from the study site.

Prior to release, subjects were evaluated to ensure it was safe for them to be released from the study site.

Subjects were released from the study site at approximately 24 hours after dose administration.

Oral Irritation Assessments

Immediately prior to the first dose (0 hour) of each oral spray treatment, including placebo administration and at time intervals as specified below, each volunteer's oral cavity was assessed for local irritation. Local irritation was evaluated relative to the zero hour observation. Whenever possible, the same evaluator performed all of the evaluations for a single subject throughout all study periods. If irritation was found, a specific description defining the location, degree, and extent of irritation was given. Irritation assessment information and time to irritation resolution was recorded in the CRF.

Irritation Assessment Schedule

Irritation assessments were collected at the following time points: Prior to each oral spray administration, immediately after swallowing (2 minutes), and at 1 hour post administration.

If any irritation persisted beyond the one hour assessment, assessments continued every two hours until resolution up to ten hours post-dose. If irritation was still reported at ten hours, the subject was assessed by the Investigator as to whether the subject should be discontinued from the study. Any assessments after one hour also included a subjective evaluation question.

Irritation Assessment

The examination consisted of a visual inspection/evaluation of the soft tissue for irritation of the labial and buccal mucosa and tongue. The time and date of these examinations was recorded. A small flashlight or other similar device was used to facilitate the examinations. The oral mucosa surfaces, right and left, and labial junctions and tongue were examined for irritation and graded according to the following classification system.

Irritation Assessment Scale

Numerical Grade Erythema—Oral Mucosa (Left and Right) and Tongue

0 No erythema

1 Very slight erythema (barely perceptible)

2 Slight erythema (edges of area well defined by definite raising)

3 Moderate erythema (raised approximately 1.0 mm)
4 Severe erythema (raised more than 1.0 mm extending beyond the area of exposure)

Study Subjects
Disposition of Subjects

Twenty-eight (28) volunteers checked in for Period I and a total of 24 subjects were enrolled. The study was conducted with 24 (23 completed) healthy adult males.

Subjects checked into the clinical facility on 30 Jul. 2010 for Period I, on 6 Aug. 2010 for Period II, on 13 Aug. 2010 for Period III, and on 20 Aug. 2010 for Period IV. Check-in occurred two days prior to dose administration for Period I and one day prior to dose administration for Periods II, III, and IV. The subjects remained confined at the clinical facility until after the 24-hour blood sample collection of each period.

Table 6.1-1 presents all discontinued subjects, the reason(s) for discontinuation, and time points during the study at which each subject was discontinued.

TABLE 6.1-1

Discontinued Subjects

| Subject No. | Reason | Gender | Age | Race |
|---|---|---|---|---|
| 24 | Withdrew prior to Period IV check-in due to personal reasons (schedule conflict) | M | 19 | American Indian or Alaskan Native |

Table 6.1-2 presents the number of subjects who were randomized according to each treatment sequence and the post-randomization discontinuation that occurred over the course of the study.

Table 6.1-3 presents the summary of subject disposition by study period.

TABLE 6.1-2

Summary of Subject Disposition by Sequence

| | Sequence | | | | |
|---|---|---|---|---|---|
| | ABCD | BDAC | CADB | DCBA | Total |
| Subjects Randomized | 6 | 6 | 6 | 6 | 24 |
| Subjects Who Successfully Completed the Study | 6 | 6 | 5 | 6 | 23 |
| Subjects Who Withdrew Consent | 0 | 0 | 1 | 0 | 1 |
| Subjects Discontinued by the Sponsor | 0 | 0 | 0 | 0 | 0 |
| Subjects Excluded from PK Analysis | 0 | 0 | 1 | 0 | 1 |

Treatment A: Sildenafil Citrate Oral Spray 11.55% w/w (1 spray, eqUlvalent to 10 mg slldenafil);
Treatment B: Sildenafil Citrate Oral Spray 11.55% w/w (2 sprays, equivalent to 20 mg sildenafil);
Treatment C: Sildenafil Citrate Oral Spray 11.55% w/w (3 sprays, equivalent to 30 mg sildenafil);
Treatment D: Viagra ® tablets 25 mg

TABLE 6.1-3

Summary of Subject Disposition by Study Period

| | Total | Period I | Period II | Period III | Period IV |
|---|---|---|---|---|---|
| Number of Subjects Randomized | 24 | 24 | 24 | 24 | 23 |
| Number of Subjects Who Completed the Period/Study | 23 | 24 | 24 | 24 | 23 |

TABLE 6.1-3-continued

Summary of Subject Disposition by Study Period

| | Total | Period I | Period II | Period III | Period IV |
|---|---|---|---|---|---|
| Number of Subjects Discontinued by Medical Investigator | 0 | 0 | 0 | 0 | 0 |
| Number of Subjects Discontinued by the Sponsor | 0 | 0 | 0 | 0 | 0 |
| Number of Subjects Who Withdrew | 1 | 0 | 0 | 0 | 1 |

Pharmacokinetic Evaluations
Data Sets Analyzed

Twenty-four (24) subjects were enrolled in the study and all subjects were healthy adults.

Twenty-four (24) subjects began the study and 23 subjects completed the clinical portion of the study in its entirety.

Data for all 24 subjects were used in the statistical analysis for sildenafil and N-desmethylsildenafil for the Test Product A (1 Spray; 10 mg) versus Reference Product D (1 Tablet, 25 mg) comparisons and Test Product C (3 Sprays; 30 mg) versus Reference Product D (1 Tablet, 25 mg) comparisons. Subject 24 elected to withdraw from the study prior to Period IV check-in due to a schedule conflict. Data for 23 of 24 subjects were used in the statistical analysis for sildenafil and N-desmethylsildenafil for the Test Product B (2 Sprays; 20 mg) versus Reference Product D (1 Tablet, 25 mg) comparisons. Actual times were used in the calculation of pharmacokinetic parameters.

Bioanalytical Method Summary

The bioanalytical laboratory of Cetero Research—Toronto determined the sildenafil and N-desmethylsildenafil plasma concentrations. The analysis was performed on a Micromass Quattro Ultima LC/MS/MS system, equipped with Z-spray. The positive ions were measured in MRM mode. The analyte was quantitated using a liquid-liquid extraction procedure. Following extraction, a 20 μL aliquot was injected onto an LC/MSIMS system. The data was acquired by, and calculated on, Micromass "Mass lynx" software version 4.1. Linear regression with $1/x^2$ weighting was used to obtain the best fit of the data for the calibration curve. The lower limit of quantitation (LLOQ) was 1.000/0.2500 ng/mL and the upper limit of quantitation (ULOQ) was 300.0/75.00 ng/mL for sildenafill N-desmethylsildenafil. Calibration curve standards and quality control (QC) samples for sildenafil and N-desmethylsildenafil met the acceptance criteria for the runs used for the final data, demonstrating satisfactory performance of the method during the analysis of study subject samples.

Pharmacokinetic Results and Tabulations of Individual Subject Data Statistical Analytical Issues The pharmacokinetic parameters were calculated using WinNonlin®, Version 5.0.1, software designed specifically for analyzing pharmacokinetic data. WinNonlin® Model 200 for extravascular input was utilized.

An Analysis of Variance (ANOV A) was performed on each of the pharmacokinetic parameters using SAS® software. The ANOV A model containing factors for sequence of products, subjects within sequence, periods and products was utilized in comparing the effects between the test and reference products.

Handling of Dropouts or Missing Data

Plasma level data from subjects who completed the study were included in the final data analysis. Plasma level data from subjects who withdrew or were discontinued for any reason were not used in the final analysis. Data from subjects with missing concentration values (e.g., missed blood draws, lost samples, samples unable to be quantified) were used if pharmacokinetic parameters could be estimated using remaining data points; otherwise, data from these subjects were excluded from the final analysis.

Pharmacokinetic Results

Sildenafil (Non-Dose-Adjusted)

Table 7.2.6.1-1 summarizes the non-dose-adjusted sildenafil pharmacokinetic parameters for each product using noncompartmental analysis.

TABLE 7.2.6.1-1

Summary Statistics and Pharmacokinetic Parameter Values for Non-Dose-Adjusted Sildenafil Data for the Noncompartmental Analysis

| | Arithmetic Mean (% CV) Median (Range) for $T_{max}$ | | | |
|---|---|---|---|---|
| Parameter | Test Product A (1 Spray; 10 mg) | Test Product B (2 Sprays; 20 mg) | Test Product C (3 Sprays; 30 mg) | Reference Product D (1 Tablet, 25 mg) |
| $AUC_{0-t}$ (ng · hr/mL) | 137.53 (70.51) | 267.73 (44.86) | 393.86 (39.88) | 294.43 (49.18) |
| $AUC_{0-inf}$ (ng · hr/mL) | 142.33 (69.56) | 274.15 (44.36) | 401.20 (39.62) | 301.24 (48.90) |
| $C_{max}$ (ng/mL) | 44.48 (68.35) | 85.86 (45.35) | 123.91 (38.90) | 107.46 (51.32) |
| $T_{max}$ (hr) | 1.00 (0.50-3.00) | 1.00 (0.33-2.05) | 1.00 (0.50-2.00) | 0.75 (0.50-2.00) |
| Kel (1/hr) | 0.3359 (27.03) | 0.2784 (34.05) | 0.2498 (36.79) | 0.2681 (36.08) |
| $T_{1/2}$ (hr) | 2.25 (32.36) | 2.78 (34.02) | 3.14 (34.73) | 2.95 (39.82) |

Treatment A: Sildenafil Citrate Oral Spray 11.55% w/w (1 spray, equivalent to 10 mg sildenafil);
Treatment B: Sildenafil Citrate Oral Spray 11.55% w/w (2 sprays, equivalent to 20 mg sildenafil);
Treatment C: Sildenafil Citrate Oral Spray 11.55% w/w (3 sprays, equivalent to 30 mg sildenafil);
Treatment D: Viagra ® tablets 25 mg Overall, plasma sildenafil concentrations were well characterized at the 10 mg, 20 mg, and 30 mg oral spray doses and at the 25 mg oral tablet dose, and declined in a monoexponential manner following oral sprays and oral tablet administration in healthy adult male volunteers.

In general, when oral spray sildenafil 10 mg, 20 mg, and 30 mg test products were administered to healthy adult males, the overall extent of sildenafil exposure and peak plasma concentrations, as assessed by mean AUC and $C_{max}$, respectively, increased proportionally with increasing doses from 10 mg to 30 mg. For all treatments, maximum sildenafil concentrations tended to be rapidly reached by approximately 1.00 hour after dose. The mean terminal half-lives values were, in general, similar for all four treatments, with estimated mean half-lives between 2.25 and 3.14 hours.

Tables 7.2.6.1-2, 7.2.6.1-3, and 7.2.6.1-4 summarize the results of the analyses performed on the pharmacokinetic parameters for non-dose-adjusted sildenafil.

TABLE 7.2.6.1-2

Geometric Means, Ratios of Means, and 90% Confidence Intervals of Ln-Transformed Non-Dose Adjusted Sildenafil Data for Test Product A (1 Spray; 10 mg) versus Reference Product D (25 mg); (N = 24)

| Parameter | Test A | Reference D | % Ratio | 90% CI |
|---|---|---|---|---|
| $C_{max}$ (ng/mL) | 38.46 | 96.97 | 39.66 | (35.34, 44.51) |
| $AUC_{0-t}$ (ng-hr/mL) | 119.75 | 266.13 | 44.99 | (41.28, 49.05) |
| $AUC_{0-inf}$ (ng-hr/mL) | 124.24 | 272.68 | 45.56 | (41.84, 49.62) |

TABLE 7.2.6.1-2-continued

Geometric Means, Ratios of Means, and 90% Confidence Intervals of Ln-Transformed Non-Dose Adjusted Sildenafil Data for Test Product A (1 Spray; 10 mg) versus Reference Product D (25 mg); (N = 24)

| Parameter | Test A | Reference D | % Ratio | 90% CI |
|---|---|---|---|---|

Treatment A: Sildenafil Citrate Oral Spray 11.55% w/w (1 spray, equivalent to 10 mg sildenafil);
Treatment D: Viagra@ tablets 25 mg

TABLE 7.2.6.1-3

Geometric Means, Ratios of Means, and 90% Confidence Intervals of Ln-Transformed Non-Dose Adjusted Sildenafil Data for Test Product B (2 Sprays; 20 mg) versus Reference Product D (25 mg); (N = 23)

| Parameter | Test B | Reference D | % Ratio | 90% CI |
|---|---|---|---|---|
| $C_{max}$ (ng/mL) | 82.26 | 97.13 | 84.69 | (75.40, 95.13) |
| $AUC_{0-t}$ (ng-hr/mL) | 258.53 | 266.84 | 96.89 | (88.82, 105.68) |
| $AUC_{0-inf}$ (ng-hr/mL) | 264.97 | 273.35 | 96.94 | (88.96, 105.63) |

Treatment B: Sildenafil Citrate Oral Spray 11.55% w/w (2 sprays, equivalent to 20 mg sildenafil);
Treatment D: Viagra ® tablets 25 mg

TABLE 7.2.6.1-4

Geometric Means, Ratios of Means, and 90% Confidence Intervals of Ln-Transformed Non-Dose Adjusted Sildenafil Data for Test Product C (3 Sprays; 30 mg) versus Reference Product D (25 mg); (N = 24)

| Parameter | Test C | Reference D | % Ratio | 90% CI |
|---|---|---|---|---|
| $C_{max}$ (ng/mL) | 114.84 | 96.97 | 118.42 | (105.52, 132.90) |
| $AUC_{0-t}$ (ng-hr/mL) | 365.98 | 266.13 | 137.52 | (126.15, 149.90) |
| $AUC_{0-inf}$ (ng-hr/mL) | 373.26 | 272.68 | 136.89 | (125.70, 149.07) |

Treatment C: Sildenafil Citrate Oral Spray 11.55% w/w (3 sprays, equivalent to 30 mg sildenafil);
Treatment D: Viagra ® tablets 25 mg When PK parameters AUC and $C_{max}$ for oral spray products Test A (10 mg), Test B (20 mg), and Test C (30 mg) were not dose-adjusted to the Reference D tablet (25 mg), the relative bioavailability of sildenafil in the test oral spray products as compared to the reference tablet product demonstrated that:

The non-dose adjusted AUCs of sildenafil for the 2 spray (20 mg dose) Test B product were comparable to the 25 mg tablet Reference D product. The point estimate for $C_{max}$ was approximately 15% lower than the 25 mg Reference D tablet and the lower limit of the 90% CI for $C_{max}$ was only slightly below the lower acceptance range at 75.40%.

As expected, the AUCs and $C_{max}$ values for the 1 spray (10 mg dose) Test A product were significantly lower, and for the 3 spray (30 mg dose) Test C product were significantly higher than the Reference D product (25 mg tablet).

Sildenafil (Dose-Adjusted)

Table 7.2.6.2-1 presents a summary of the dose-adjusted sildenafil pharmacokinetic parameters for each product using noncompartmental analysis.

TABLE 7.2.6.2-1

Summary Statistics and Pharmacokinetic Parameter Values for Dose-Adjusted Sildenafil Data for the Noncompartmental Analysis

| Parameter | Arithmetic Mean (% CV) Median (Range) for $T_{max}$ | | | |
|---|---|---|---|---|
| | Test Product A (1 Spray; 10 mg) | Test Product B (2 Sprays; 20 mg) | Test Product C (3 Sprays; 30 mg) | Reference Product D (1 Tablet, 25 mg) |
| $AUC_{0-t}$ (ng · hr/mL) | 343.83 (70.51) | 334.66 (44.86) | 328.21 (39.88) | 294.43 (49.18) |
| $AUC_{0-inf}$ (ng · hr/mL) | 355.82 (69.56) | 342.69 (44.36) | 334.33 (39.62) | 301.24 (48.90) |
| $C_{max}$ (ng/mL) | 111.19 (68.35) | 107.32 (45.35) | 103.26 (38.90) | 107.46 (51.32) |

Treatment A: Sildenafil Citrate Oral Spray 11.55% w/w (1 spray, equivalent to 10 mg sildenafil);
Treatment B: Sildenafil Citrate Oral Spray 11.55% w/w (2 sprays, equivalent to 20 mg siidenafil);
Treatment C: Sildenafil Citrate Oral Spray 11.55% w/w (3 sprays, equivalent to 30 mg sildenafil);
Treatment D: Viagra ® tablets 25 mg The dose-adjusted $C_{max}$ for the sildenafil oral spray products Test A (10 mg), Test B (20 mg), and Test C (30 mg) was comparable to the Reference D tablet (25 mg), whereas overall extent of sildenafil exposure as assessed by dose-adjusted AUC was consistently higher than the Reference D tablet (25 mg) with $AUC_{0-t}$ range of 328 to 344 ng-hr/mL for the oral spray compared to 294 ng-hr/mL for the reference 25 mg tablet and with $AUC_{0-inf}$ range of 334 to 356 ng-hr/mL for the oral spray compared to 301 ng-hr/mL for the reference 25 mg tablet.

The peak plasma concentrations, as assessed by $C_{max}$, were comparable across all test doses (oral spray of 10 mg, 20 mg, and 30 mg) to the reference dose (oral tablet of 25 mg). For all treatments, the peak plasma concentrations ranged from 103.26 ng/mL-111.19 ng/mL.

Tables 7.2.6.2-2, 7.2.6.2-3, and 7.2.6.2-4 summarize the results of the analyses performed on the pharmacokinetic parameters for dose-adjusted sildenafil

TABLE 7.2.6.2-2

Geometric Means, Ratios of Means, and 90% Confidence Intervals of Ln-Transformed Dose-Adjusted Sildenafil Data for Test Product A (1 Spray; 10 mg) versus Reference Product D (25 mg); (N = 24)

| Parameter | Test A | Reference D | % Ratio | 90% CI |
|---|---|---|---|---|
| $C_{max}$ (ng/mL) | 96.16 | 96.97 | 99.16 | (88.36, 111.28) |
| $AUC_{0-t}$ (ng-hr/mL) | 299.36 | 266.20 | 112.46 | (103.16, 122.59) |
| $AUC_{0-inf}$ (ng-hr/mL) | 310.60 | 272.74 | 113.88 | (104.57, 124.02) |

Treatment A: Sildenafil Citrate Oral Spray 11.55% w/w (1 spray, equivalent to 10 mg sildenafil);
Treatment D: Viagra ® tablets 25 mg

TABLE 7.2.6.2-3

Geometric Means, Ratios of Means, and 90% Confidence Intervals of Ln-Transformed Dose-Adjusted Sildenafil Data for Test Product B (2 Sprays; 20 mg) versus Reference Product D (25 mg); (N = 23)

| Parameter | Test B | Reference D | % Ratio | 90% CI |
|---|---|---|---|---|
| $C_{max}$ (ng/mL) | 102.83 | 97.13 | 105.87 | (94.25, 118.92) |
| $AUC_{0-t}$ (ng-hr/mL) | 323.16 | 266.91 | 121.08 | (111.00, 132.07) |
| $AUC_{0-inf}$ (ng-hr/mL) | 331.22 | 273.41 | 121.14 | (111.17, 132.01) |

Treatment B: Sildenafil Citrate Oral Spray 11.55% w/w (2 sprays, equivalent to 20 mg sildenafil);
Treatment D: Viagra ® tablets 25 mg

TABLE 7.2.6.2-4

Geometric Means, Ratios of Means, and 90% Confidence Intervals of Ln-Transformed Dose-Adjusted Sildenafil Data for Test Product C (3 Sprays; 30 mg) versus Reference Product D (25 mg); (N = 24)

| Parameter | Test C | Reference D | % Ratio | 90% CI |
|---|---|---|---|---|
| $C_{max}$ (ng/mL) | 95.70 | 96.97 | 98.69 | (87.94, 110.75) |
| $AUC_{0-t}$ (ng-hr/mL) | 304.98 | 266.20 | 114.57 | (105.10, 124.89) |
| $AUC_{0-inf}$ (ng-hr/mL) | 311.05 | 272.74 | 114.04 | (104.72, 124.20) |

Treatment C: Sildenafil Citrate Oral Spray 11.55% w/w (3 sprays, equivalent to 30 mg sildenafil);
Treatment D: Viagra ® tablets 25 mg When PK parameters AUC and $C_{max}$ for oral spray products Test A (10 mg), Test B (20 mg), and Test C (30 mg) were dose-adjusted to the Reference D tablet (25 mg), the relative bioavailability of sildenafil in the test oral spray products as compared to the reference tablet product demonstrated that:

The dose-adjusted $C_{max}$ values of sildenafil for the 10 mg, 20 mg, and 30 mg oral spray products were comparable to the Reference D product (25 mg tablet) and all were within the 90% CI.

The Test/Reference ratio point estimates for the dose-adjusted $AUC_{0-inf}$ for all the sildenafil oral spray doses were approximately 114% to 121%. The upper limit of the 90% CI was 124% for Test A (10 mg) and Test C (30 mg) doses, just below the 125% upper limit. The Test/Reference ratio point estimates for the dose-adjusted $AUC_{0-t}$ for all the sildenafil oral spray doses were approximately 112% to 121%. The upper limit of the 90% CI was 123% for Test A (10 mg) and 125% for Test C (30 mg) doses. For the Test B (20 mg) oral spray, the point estimates for AUCs were approximately 21% higher and the 90% CI for AUCs were above the upper acceptance range at 132%.

These data indicate that the overall systemic sildenafil exposure for the oral spray test product is more systemically bioavailable than the 25 mg oral tablet reference product, likely due to avoiding first pass metabolism through transmucosal absorption.

N-desmethylsildenafil (Non-Dose-Adjusted)

Table 7.2.6.3-1 presents a summary of the non-dose-adjusted N-desmethylsildenafil pharmacokinetic parameters for each product using noncompartmental analysis.

TABLE 7.2.6.3-1

Summary Statistics and Pharmacokinetic Parameter Values for Non-Dose-Adjusted N-desmethylsildenafil Data for the Noncompartmental Analysis

| Parameter | Arithmetic Mean (% CV) Median (Range) for $T_{max}$ | | | |
|---|---|---|---|---|
| | Test Product A (1 Spray; 10 mg) | Test Product B (2 Sprays; 20 mg) | Test Product C (3 Sprays; 30 mg) | Reference Product D (1 Tablet, 25 mg) |
| $AUC_{0-t}$ (ng · hr/mL) | 30.57 (41.21) | 68.79 (37.52) | 110.03 (36.06) | 86.74 (31.44) |
| $AUC_{0-inf}$ (ng · hr/mL) | 32.18 (40.51) | 71.58 (37.10) | 113.10 (35.72) | 89.34 (31.11) |
| $C_{max}$ (ng/mL) | 8.78 (34.19) | 20.05 (36.47) | 30.68 (30.52) | 29.04 (38.26) |
| $T_{max}$ (hr) | 1.00 (0.33-2.00) | 1.00 (0.50-2.05) | 1.00 (0.50-2.00) | 0.75 (0.50-2.00) |
| Kel (1/hr) | 0.2407 (26.65) | 0.1828 (33.77) | 0.1606 (29.29) | 0.1695 (25.90) |

TABLE 7.2.6.3-1-continued

Summary Statistics and Pharmacokinetic Parameter
Values for Non-Dose-Adjusted N-desmethylsildenafil
Data for the Noncompartmental Analysis

|  | Arithmetic Mean (% CV) Median (Range) for $T_{max}$ | | | |
|---|---|---|---|---|
| Parameter | Test Product A (1 Spray; 10 mg) | Test Product B (2 Sprays; 20 mg) | Test Product C (3 Sprays; 30 mg) | Reference Product D (1 Tablet, 25 mg) |
| $T_{1/2}$ (hr) | 3.22 (47.61) | 4.27 (35.61) | 4.66 (27.37) | 4.42 (30.71) |

Treatment A: Sildenafil Citrate Oral Spray 11.55% w/w (1 spray, equivalent to 10 mg sildenafil);
Treatment B: Sildenafil Citrate Oral Spray 11.55% w/w (2 sprays, equivalent to 20 mg sildenafil);
Treatment C: Sildenafil Citrate Oral Spray 11.55% w/w (3 sprays, equivalent to 30 mg siidenafil);
Treatment D: Viagra ® tablets 25 mg In general, the overall extent of N-desmethylsildenafil exposure and peak plasma concentrations for oral spray products Test A (10 mg), Test B (20 mg), and Test C (30 mg), as assessed by mean AUCs and $C_{max}$, increased proportionally with increasing doses from 10 mg to 30 mg. For all doses of the sildenafil oral spray treatments, the time to reach maximum N-desmethylsildenafil concentrations was slightly slower than the oral tablet reference product $T_{max}$ of 0.75 hours; however, the ranges of $T_{max}$ for all test sildenafil oral sprays and the reference oral tablet were similar. The mean terminal half-life values were, in general, similar for all four treatments.

Tables 7.2.6.3-2, 7.2.6.3-3, and 7.2.6.3-4 summarize the results of the analyses performed on the pharmacokinetic parameters for non-dose-adjusted N-desmethylsildenafil

TABLE 7.2.6.3-2

Geometric Means, Ratios of Means, and 90% Confidence Intervals
of Ln-Transformed N-desmethylsildenafil Data for Test Product A
(1 Spray; 10 mg) versus Reference Product D (25 mg); (N = 24)

| Parameter | Test A | Reference D | % Ratio | 90% CI |
|---|---|---|---|---|
| $C_{max}$ (ng/mL) | 8.31 | 26.95 | 30.84 | (28.17, 33.76) |
| $AUC_{0-t}$ (ng-hr/mL) | 28.27 | 81.90 | 34.51 | (32.12, 37.08) |
| $AUC_{0-inf}$ (ng-hr/mL) | 29.87 | 84.49 | 35.35 | (32.98, 37.89) |

Treatment A: Sildenafil Citrate Oral Spray 11.55% w/w (1 spray, equivalent to 10 mg sildenafil);
Treatment D: Viagra ® tablets 25 mg

TABLE 7.2.6.3-3

Geometric Means, Ratios of Means, and 90% Confidence Intervals
of Ln-Transformed N-desmethylsildenafil Data for Test Product B
(2 Sprays; 20 mg) versus Reference Product D (25 mg); (N = 23)

| Parameter | Test B | Reference D | % Ratio | 90% CI |
|---|---|---|---|---|
| $C_{max}$ (ng/mL) | 18.91 | 27.08 | 69.84 | (63.76, 76.49) |
| $AUC_{0-t}$ (ng-hr/mL) | 65.07 | 82.68 | 78.71 | (73.27, 84.54) |
| $AUC_{0-inf}$ (ng-hr/mL) | 67.84 | 85.28 | 79.54 | (74.24, 85.23) |

Treatment B: Sildenafil Citrate Oral Spray 11.55% w/w (2 sprays, equivalent to 20 mg sildenafil);
Treatment D: Viagra ® tablets 25 mg

TABLE 7.2.6.3.4

Geometric Means, Ratios of Means, and 90% Confidence Intervals
of Ln-Transformed N-desmethylsildenafil Data for Test Product C
(3 Sprays; 30 mg) versus Reference Product D (25 mg); (N = 24)

| Parameter | Test C | Reference D | % Ratio | 90% CI |
|---|---|---|---|---|
| $C_{max}$ (ng/mL) | 29.28 | 26.95 | 108.65 | (99.25, 118.94) |
| $AUC_{0-t}$ (ng-hr/mL) | 102.91 | 81.90 | 125.65 | (116.95, 134.99) |
| $AUC_{0-inf}$ (ng-hr/mL) | 105.88 | 84.49 | 125.32 | (116.93, 134.31) |

Treatment C: Sildenafil Citrate Oral Spray 11.55% w/w (3 sprays, equivalent to 30 mg sildenafil);
Treatment D: Viagra ® tablets 25 mg When N-desmethylsildenafil PK parameters AUC and $C_{max}$ for oral spray products Test A (10 mg), Test B (20 mg), and Test C (30 mg) were not dose-adjusted to the Reference D tablet (25 mg), the relative bioavailability of N-desmethylsildenafil in the test oral spray products as compared to the reference tablet product demonstrated that:

The point estimates for non-dose-adjusted AUCs of N-desmethylsildenafil between the 10 mg, 20 mg, and 30 mg test oral spray doses were, in general, comparable to the difference to the 25 mg reference tablet.

The point estimates for $C_{max}$ between the 10 mg, 20 mg, and 30 mg test oral spray doses were generally less than the difference to the 25 mg reference oral tablet.

N-desmethylsildenafil (Dose-Adjusted)

Table 7.2.6.4-1 presents a summary of the dose-adjusted N-desmethylsildenafil pharmacokinetic parameters for each product using noncompartmental analysis.

TABLE 7.2.6.4-1

Summary Statistics and Pharmacokinetic Parameter Values
for Dose-Adjusted N-desmethylsildenafil Data for the
Noncompartmental Analysis

|  | Arithmetic Mean (% CV) Median (Range) for $T_{max}$ | | | |
|---|---|---|---|---|
| Parameter | Test Product A (1 Spray; 10 mg) | Test Product B (2 Sprays; 20 mg) | Test Product C (3 Sprays; 30 mg) | Reference Product D (1 Tablet; 25 mg) |
| $AUC_{0-t}$ (ng · hr/mL) | 76.44 (41.21) | 85.99 (37.52) | 91.69 (36.06) | 86.74 (31.44) |
| $AUC_{0-inf}$ (ng · hr/mL) | 80.46 (40.51) | 89.47 (37.10) | 94.25 (35.72) | 89.34 (31.11) |
| $C_{max}$ (ng/mL) | 21.94 (34.19) | 25.06 (36.47) | 25.57 (30.52) | 29.04 (38.26) |

Treatment A: Sildenafil Citrate Oral Spray 11.55% w/w (1 spray, equivalent to to mg sildenafil);
Treatment B: Sildenafil Citrate Oral Spray 11.55% w/w (2 sprays, equivalent to 20 mg siidenafil);
Treatment C: Sildenafil Citrate Oral Spray 11.55% w/w (3 sprays, equivalent to 30 mg sildenafil);
Treatment D: Viagra ® tablets 25 mg After dose-adjusting the PK parameters AUC and $C_{max}$ of N-desmethylsildenafil for oral spray products Test A (10 mg), Test B (20 mg), and Test C (30 mg) to the Reference D tablet (25 mg), the overall extent of exposure of N-desmethylsildenafil, as assessed by AUC, shows a trend to slightly increase with increasing doses from 10 mg to 30 mg. However, the dose-adjusted peak N-desmethylsildenafil plasma concentrations, as assessed by $C_{max}$, were similar for the test oral spray doses of 20 mg and 30 mg, but slightly less for the test oral spray dose of 10 mg. For all four products, the peak plasma concentrations ranged from 21.94 ng/mL-29.04 ng/mL.

Tables 7.2.6.4-2, 7.2.6.4-3, and 7.2.6.4-4 summarize the results of the analyses performed on the pharmacokinetic parameters for dose-adjusted N-desmethylsildenafil.

TABLE 7.2.6.4-2

Geometric Means, Ratios of Means, and 90% Confidence Intervals of Dose-Adjusted Ln-Transformed N-desmethyl-sildenafil Data for Test Product A (1 Spray; 10 mg) versus Reference Product D (25 mg); (N = 24)

| Parameter | Test A | Reference D | % Ratio | 90% CI |
|---|---|---|---|---|
| $C_{max}$ (ng/mL) | 20.78 | 26.95 | 77.09 | (70.42, 84.40) |
| $AUC_{0-t}$ (ng-hr/mL) | 70.67 | 81.90 | 86.28 | (80.31, 92.70) |
| $AUC_{0-inf}$ (ng-hr/mL) | 74.67 | 84.49 | 88.38 | (82.46, 94.72) |

Treatment A: Sildenafil Citrate Oral Spray 11.55% w/w (1 spray, equivalent to 10 mg sildenafil);
Treatment D: Viagra ® tablets 25 mg

TABLE 7.2.6.4-3

Geometric Means, Ratios of Means, and 90% Confidence Intervals of Ln-Transformed Dose-Adjusted N-desmethyl-sildenafil Data for Test Product B (2 Sprays; 20 mg) versus Reference Product D (25 mg); (N = 23)

| Parameter | Test B | Reference D | % Ratio | 90% CI |
|---|---|---|---|---|
| $C_{max}$ (ng/mL) | 23.64 | 27.08 | 87.29 | (79.70, 95.62) |
| $AUC_{0-t}$ (ng-hr/mL) | 81.34 | 82.68 | 98.38 | (91.59, 105.68) |
| $AUC_{0-inf}$ (ng-hr/mL) | 84.80 | 85.28 | 99.43 | (92.80, 106.54) |

Treatment B: Sildenafil Citrate Oral Spray 11.55% w/w (2 sprays, equivalent to 20 mg sildenafil);
Treatment D: Viagra ® tablets 25 mg

TABLE 7.2.6.4-4

Geometric Means, Ratios of Means, and 90% Confidence Intervals of Ln-Transformed Dose-Adjusted N-desmethyl-sildenafil Data for Test Product C (3 Sprays; 30 mg) versus Reference Product D (25 mg); (N = 24)

| Parameter | Test C | Reference D | % Ratio | 90% CI |
|---|---|---|---|---|
| $C_{max}$ (ng/mL) | 24.40 | 26.95 | 90.55 | (82.71, 99.12) |
| $AUC_{0-t}$ (ng-hr/mL) | 85.76 | 81.90 | 104.71 | (97.46, 112.49) |
| $AUC_{0-inf}$ (ng-hr/mL) | 88.23 | 84.49 | 104.43 | (97.44, 111.92) |

Treatment C: Sildenafil Citrate Oral Spray 11.55% w/w (3 sprays, equivalent to 30 mg sildenafil);
Treatment D: Viagra ® tablets 25 mg After dose-adjusting the PK parameters AUC and $C_{max}$ of N-desmethylsildenafil for oral spray products Test A (10 mg), Test B (20 mg), and Test C (30 mg) to the Reference D tablet (25 mg), the PK and statistical results demonstrated that, with the exception of the $C_{max}$ for the test oral spray 10 mg and 20 mg doses, the AUCs and $C_{max}$ values were all within the 90% CI criteria of 80%-125%.

Dose Proportionality

The results for dose proportionality at doses of single 10 mg, 20 mg, and 30 mg oral spray administrations of sildenafil demonstrate that, while the $AUC_{inf}$ increases linearly with dose, it does not do so in exactly a dose proportional manner; specifically, a slightly greater than dose-proportional increase is observed. As the results in the Table 7.2.6.5-1 demonstrate, a mean 2.24 and 3.13 fold increase in $AUC_{inf}$ is observed from 1 to 2 sprays and 1 to 3 sprays, respectively. Similar greater than non-proportional dose results following single oral dose administration of sildenafil tablets in healthy male volunteers have been reported by Nichols et al. and, as noted in that study and in this study, the extent of this non-proportionality is unlikely to be clinically significant.

TABLE 7.2.6.5-1

Dose Proportionality for Sildenafil Test Oral Spray

| | Test A to Test B (1 to 2 Sprays) | Test A to Test C (1 to 3 Sprays) |
|---|---|---|
| Theory | 2 | 3 |
| Observed Mean Ind. | 2.24 | 3.13 |
| Standard Deviation | 0.50 | 0.85 |
| % CV | 22.31 | 27.23 |

Treatment A: Sildenafil Citrate Oral Spray 11.55% w/w (1 spray, eqUIvalent to 10 mg sildenafil);
Treatment B: Sildenafil Citrate Oral Spray 11.55% w/w (2 sprays, equivalent to 20 mg siidenafil);
Treatment C: Sildenafil Citrate Oral Spray 11.55% w/w (3 sprays, equivalent to 30 mg siidenafil)

Metabolite/Parent Ratio (N-desmethylsildenafil/Sildenafil Ratio)

Table 7.2.6.6-1 summarizes the Metabolite/Parent Ratio (N-desmethylsildenafil/Sildenafil) pharmacokinetic parameters for each treatment test product.

TABLE 7.2.6.6-1

Summary Statistics and Pharmacokinetic Parameter Values for Metabolite/Parent Ratio (N-desmethylsildenafil/Sildenafil)

| | Arithmetic Mean (% CV) | | | |
|---|---|---|---|---|
| Parameter | Test Product A (1 Spray; 10 mg) | Test Product B (2 Sprays; 20 mg) | Test Product C (3 Sprays; 30 mg) | Reference Product D (1 Tablet, 25 mg) |
| $AUC_{0-t}$ | 0.26 (41.90) | 0.28 (38.01) | 0.30 (35.76) | 0.34 (46.49) |
| $AUC_{0-inf}$ | 0.26 (40.42) | 0.28 (37.18) | 0.30 (35.39) | 0.34 (45.97) |
| $C_{max}$ | 0.24 (45.81) | 0.26 (45.40) | 0.27 (33.68) | 0.31 (48.46) |

Treatment A: Sildenafil Citrate Oral Spray 11.55% w/w (1 spray, equivalent to 10 mg siidenafil);
Treatment B: Sildenafil Citrate Oral Spray 11.55% w/w (2 sprays, equivalent to 20 mg sildenafil);
Treatment C: Sildenafil Citrate Oral Spray 11.55% w/w (3 sprays, equivalent to 30 mg sildenafil);
Treatment D: Viagra ® tablets 25 mg Tables 7.2.6.6-2, 7.2.6.6-3, and 7.2.6.6-4 summarize the results of the analyses performed on the pharmacokinetic parameters for N-desmethylsildenafil/Sildenafil Ratio.

TABLE 7.2.6.6-2

Geometric Means, Ratios of Means, and 90% Confidence Intervals of Ln-Transformed N-desmethylsildenafil/Sildenafil Ratio for Test Product A (1 Spray; 10 mg) versus Reference Product D (25 mg); (N = 24)

| Parameter | Test A | Reference D | % Ratio | 90% CI |
|---|---|---|---|---|
| $C_{max}$ | 0.22 | 0.28 | 77.84 | (71.32, 84.96) |
| $AUC_{0-t}$ | 0.24 | 0.31 | 76.56 | (71.78, 81.66) |
| $AUC_{0-inf}$ | 0.24 | 0.31 | 77.85 | (73.01, 83.01) |

Treatment A: Sildenafil Citrate Oral Spray 11.55% w/w (1 spray, equivalent to 10 mg siidenafil);
Treatment D: Viagra ® tablets 25 mg

TABLE 7.2.6.6-3

Geometric Means, Ratios of Means, and 90% Confidence
Intervals of Ln-Transformed N-desmethylsildenafil/
Sildenafil Ratio for Test Product B (2 Sprays; 20 mg)
versus Reference Product D (25 mg); (N = 23)

| Parameter | Test B | Reference D | % Ratio | 90% CI |
|---|---|---|---|---|
| $C_{max}$ | 0.23 | 0.28 | 82.71 | (75.72, 90.34) |
| $AUC_{0-t}$ | 0.25 | 0.31 | 80.97 | (75.92, 86.36) |
| $AUC_{0-inf}$ | 0.26 | 0.31 | 81.86 | (76.78, 87.27) |

Treatment B: Sildenafil Citrate Oral Spray 11.55% w/w (2 sprays, equivalent to 20 mg siidenafil);
Treatment D: Viagra ® tablets 25 mg

TABLE 7.2.6.6-4

Geometric Means, Ratios of Means, and 90% Confidence
Intervals of Ln-Transformed N-desmethylsildenafil/
Sildenafil Ratio for Test Product C (3 Sprays; 30 mg)
versus Reference Product D (25 mg); (N = 24)

| Parameter | Test C | Reference D | % Ratio | 90% CI |
|---|---|---|---|---|
| $C_{max}$ | 0.25 | 0.28 | 92.00 | (84.29, 100.42) |
| $AUC_{0-t}$ | 0.28 | 0.31 | 91.21 | (85.51, 97.28) |
| $AUC_{0-inf}$ | 0.28 | 0.31 | 91.67 | (85.97, 97.74) |

Treatment C: Sildenafil Citrate Oral Spray 11.55% w/w (3 sprays, equivalent to 30 mg siidenafil);
Treatment D: Viagra ® tablets 25 mg Overall, the results of metabolite to parent (M/P) ratios analysis demonstrated that the formation of the metabolite, as assessed by the M/P ratios for the Test A (10 mg) and Test B (20 mg) oral spray doses were less than the M/P ratio of the Reference D (25 mg) tablet, whereas the M/P ratios for the Test C (30 mg) oral spray dose were comparable to the M/P ratios observed for the Reference D (25 mg) tablet.

The M/P ratio for each concentration time point was calculated for each treatment and plotted versus time to visually assess the rate of formation of metabolite. This was done up to four hours post-dose. This plot is shown in Figure 7.2.6.6-1. It can be noted that there was an immediate peak in the M/P ratio for the reference oral tablet, whereas the M/P ratio with time for all doses of the test oral spray doses were significantly slower than the reference tablet. This observation indicates that there is a marked decrease in the rate of metabolite formation in the test oral spray products compared to the reference oral tablet product and indicative that the test oral spray is, for the most part, bypassing first pass metabolism due to transmucosal absorption.

Saliva pH Assessments

The transmucosal absorption of drugs may be dependent on the pH of the oral cavity when administered to patients. Therefore, in this study saliva pH was measured in healthy male adult volunteers at 2300 hours (±30 minutes) on Day −1 and on Day 1 within 30 minutes prior to teeth and tongue brushing. There was minimal change in saliva pH pre- and post-teeth and tongue brushing. Saliva pH was then measured within 30 minutes of completion of teeth and tongue brushing (~45 minutes pre-dose), and within 15 minutes prior to dosing. The pH was measured using pH test strips with a range of 5-9. No subject had a pH of 5, therefore, there was no additional testing with pH test strips with a range of 0-6. There were no appreciable differences found in saliva pH between treatments or periods at 45 minutes and 15 minutes prior to dose administration, as shown in the Table 7.2.7-1.

TABLE 7.2.7-1

Summary of Mean Saliva pH by Treatment and by Period

Mean Saliva pH, By Treatment, 45 and 15 minutes
Prior to Dose Administration

| Test A (1 spray, 10 mg) | | Test B (2 sprays, 20 mg) | | Test C (3 sprays, 30 mg) | | Reference D (1 Tablet, 25 mg) | |
|---|---|---|---|---|---|---|---|
| 45 min | 15 min | 45 min | 15 min | 45 min | 15 min | 45 min | 15 min |
| 6.3 | 6.2 | 6.3 | 6.3 | 6.4 | 6.5 | 6.3 | 6.2 |

Mean Saliva pH, By Period, 45 and 15 minutes
Prior to Dose Administration

| Period I | | Period II | | Period III | | Period IV | |
|---|---|---|---|---|---|---|---|
| 45 min | 15 min | 45 min | 15 min | 45 min | 15 min | 45 min | 15 min |
| 6.3 | 6.3 | 6.3 | 6.4 | 6.4 | 6.4 | 6.4 | 6.2 |

Treatment A: Slldenafil Citrate Oral Spray 11.55% w/w (1 spray, equivalent to 10 mg slldenafil);
Treatment B: Sildenafil Citrate Oral Spray 11.55% w/w (2 sprays, equivalent to 20 mg sildenafil);
Treatment C: Sildenafil Citrate Oral Spray 11.55% w/w (3 sprays, equivalent to 30 mg sildenafil);
Treatment D: Viagra ® tablets 25 mg Post-Dose Questionnaire Immediately after dosing was completed (2 minutes) and at 1 hour after dosing, subjects were queried on the following regarding the test product (oral spray):
Taste of the product
Willingness to take the product again
Any presence of excessive salivation

TABLE 7.2.8-1

Summary of Taste Questionnaire Results

| Test A (1 Spray) | | Test B (2 Sprays) | | Test C (3 Sprays) | |
|---|---|---|---|---|---|
| After swallowing | 1 hour post-dose | After swallowing | 1 hour post-dose | After swallowing | 1 hour post-dose |
| Mean taste score (1 = bad; 5 = very good) | | | | | |
| 2.2 | 3.0 | 1.9 | 3.0 | 1.8 | 2.9 |
| Willingness to take the product again (% Affirmative responses) | | | | | |
| 79% | 92% | 74% | 87% | 63% | 75% |
| Presence of any excessive salivation [Affirmative responses (%)] | | | | | |
| 6 of 24 (25%) | 3 of 24 (12.5%) | 9 of 23 (39%) | 3 of 23 (13%) | 12 of 24 (50%) | 2 of 24 (8%) |

Treatment A: Sildenafil Citrate Oral Spray 11.55% w/w (1 spray, eqUIvalent to 10 mg sildenafil);
Treatment B: Sildenafil Citrate Oral Spray 11.55% w/w (2 sprays, equivalent to 20 mg sildenafil);
Treatment C: Sildenafil Citrate Oral Spray 11.55% w/w (3 sprays, equivalent to 30 mg sildenafil)

Oral Irritation Assessment

The examination consisted of a visual inspection/evaluation of the soft tissue for irritation of the labial and buccal mucosa and tongue. The oral mucosal surfaces, right and left, and labial junctions and tongue were examined for irritation and graded according to the following classification system described below.
Numerical Grade Erythema—Oral Mucosa (Left and Right) and Tongue
0 No erythema
1 Very slight erythema (barely perceptible)

2 Slight erythema (edges of area well defined by definite raising)
3 Moderate erythema (raised approximately 1.0 mm)
4 Severe erythema (raised more than 1.0 mm extending beyond the area of exposure)

Evaluation of soft tissue irritation within the labial or buccal mucosa and of the tongue were done after both active and placebo dosing. Irritation assessments were collected at the following time points: Prior to each oral spray administration, immediately after swallowing (2 minutes), and at 1 hour post administration. If any irritation persisted beyond the one hour assessment, assessments continued every two hours until resolution up to ten hours post-dose. If irritation was still reported at ten hours, the subject was assessed by the Investigator as to whether the subject should be discontinued from the study. Any assessments after one hour also included a subjective evaluation question.

The results of the oral irritation assessment found no oral irritation following administration of placebo (3 sprays). Additionally, no oral irritation was found following administration of Test A (1 spray), Test B (2 sprays), or Test C (3 sprays), when observed immediately after administration (held for two minutes, then swallowed), and when observed at 1 hour post-dose.

Discussion

The dose-adjusted $C_{max}$ values of sildenafil for oral spray products Test A (10 mg), Test B (20 mg), and Test C (30 mg) were, in general, comparable to the Reference D (25 mg) oral tablet. The Test/Reference ratio point estimates for the dose-adjusted AUCs for all the sildenafil oral spray doses were approximately 112% to 121% and the 90% CI for AUCs were 124% to 132% with an upper acceptance range of 125%. In addition, the non-dose-adjusted point estimates for AUCs for the Test B 2 spray dose (20 mg) oral spray were approximately 97%, demonstrating comparable bioavailability to the Reference D (25 mg) oral tablet. These data indicate that the overall sildenafil exposure for the test oral spray product is more systemically bioavailable than the reference oral tablet, likely due to avoiding first pass metabolism through transmucosal absorption.

Sildenafil is known to be metabolized to its major metabolite N-desmethylsildenafil through first pass metabolism by more than 50% [absolute bioavailability is 41% (range 25-63%)]. The pharmacokinetic and statistical results following administration of the sildenafil oral spray in healthy adult male subjects demonstrated increased systemic exposure that can reasonably be attributed to oral transmucosal absorption processes.

The assessment of M/P ratio (metabolite (N-desmethylsildenafil) to parent (sildenafil) ratio) for the oral spray products Test A (10 mg), Test B (20 mg), and Test C (30 mg) as compared to the Reference D (25 mg) oral tablet demonstrated differences in the rate of formation of the metabolite indicative of trans mucosal absorption.

There was minimal change found in the mean saliva pH between treatments and periods in this study, therefore subject saliva pH was not likely a contributing factor in the apparent transmucosal absorption observed following the oral spray administration.

There was no oral irritation observed in any of the subjects following administration of sildenafil oral spray placebo or active doses (up to 3 sprays, 30 mg dose).

Overall, sildenafil citrate was well tolerated in doses of 10 mg, 20 mg, 30 mg, and was well tolerated as a single oral dose of 25 mg (1×25 mg tablet) administered to healthy adult subjects under fed conditions.

Example 4

Objective

The objective of the following was to evaluate the partial AUC exposures of sildenafil in the first, fourth, twelfth and twenty-fourth hour ($AUC_{0-1}$, $AUC_{0-4}$, $AUC_{0-12}$ and $AUC_{0-24}$) for the 10, 20 and 30 mg Test oral spray products to that of the 25 mg tablet Reference product of sildenafil.

Study Design

A randomized, four-way crossover design was used in this study to compare the relative bioavailability (rate and extent of absorption) of one test product at three different dose levels (10 mg, 20 mg, and 30 mg) with one reference product under fasting conditions. In this study, one test formulation at three different dose levels (10 mg, 20 mg, and 30 mg of an oral dose of Sildenafil Citrate Oral Spray 14 mg/0.12 mL were compared with VIAGRA® 25 mg Tablets.

Twenty-four healthy male adult subjects and no alternates were randomly assigned to one of four sequences of the following products:

Test Product (A): Sildenafil Citrate Oral Spray 11.55% w/w;

(1 Spray; 10 mg)

Test Product (B): Sildenafil Citrate Oral Spray 11.55% w/w;

(2 Spray; 20 mg)

Test Product (C): Sildenafil Citrate Oral Spray 11.55% w/w;

(3 Spray; 30 mg)

Reference Product (D): Viagra® tablets 25 mg;

The four sequences were as follows:

Sequence 1=ABC D

Sequence 2=BDA C

Sequence 3=CAD B

Sequence 4=DCB A

A single oral dose of test or reference product was administered to volunteers on four separate occasions under fasting conditions with at least a 3-day washout period between doses. Food and fluid intake were controlled during each confinement period.

The pharmacokinetic parameters for both non-dose adjusted and dose adjusted $AUC_{0-1}$, $AUC_{0-4}$, $AVC_{0-12}$ and $AUC_{0-24}$ of sildenafil and its metabolite, N-desmethylsildenafil were calculated using WinNonlin®, Version 5.0.1, software designed specifically for analyzing pharmacokinetic data. WinNonlin® Model 200 for extravascular input was utilized.

An analysis of variance (ANOVA) was performed on each of the partial $AVC_{0-1}$, $AUC_{0-4}$, $AUC_{0-12}$ and $AUC_{0-24}$ pharmacokinetic parameters using SAS® software. The ANOVA model containing factors for sequence of products, subjects within sequence, periods and products was utilized in comparing the effects between the test and reference products. $AUC_{0-24}$ calculation for majority of the subjects could not be calculated due to BLQ concentration values at hour 24.

Pharmacokinetic Results and Discussion

Table 1 presents a summary of the sildenafil pharmacokinetic parameters for each product using noncompartmental analysis.

TABLE 1

Summary Statistics and Partial AUC Values for Non-Dose Adjusted Sildenafil

| | Arithmetic Mean (% CV) | | | |
|---|---|---|---|---|
| Parameter | Test Product A (1 Spray; 10 mg) | Test Product B (2 Spray; 20 mg) | Test Product C (3 Spray; 30 mg) | Reference Product D (25 mg) |
| $AUC_{0-1}$ (ng · hr/mL) | 14.55 (59.09) | 38.00 (70.53) | 52.14 (68.57) | 51.89 (78.06) |
| $AUC_{0-4}$ (ng · hr/mL) | 99.13 (66.54) | 192.46 (42.74) | 279.07 (37.77) | 214.41 (48.29) |
| $AUC_{0-12}$ (ng · hr/mL) | 137.14 (68.42) | 262.86 (42.35) | 383.79 (38.10) | 288.63 (47.65) |
| $AUC_{0-24}$ (ng · hr/mL) |  () | 670.90 (***) | 661.69 (12.16) | 516.90 (46.74) |

** Not calculated due to BLQ at the 24 hour time point
Source: Tables 1.1.1-1.1.4

In general, when oral spray sildenafil 10, 20 and 30 mg Test products were administered to healthy adult males, the partial extent of sildenafil exposure as assessed by non-dose adjusted $AUC_{0-1}$, $AUC_{0-4}$, and $AUC_{0-12}$ increased proportionally with increasing doses.

The non-dose adjusted partial, AUCs of sildenafil Oral Spray and the Reference Tablet as presented in Table 1 demonstrates that partial $AUC_{0-1}$, $AUC_{0-4}$, $AUC_{0-12}$ and $AUC_{0-24}$ is consistent with the $AUC_{0-t}$ and $AUC_{0-inf}$ (Table 7.2.6.1-1) difference observed between the oral spray and reference tablet with the 2 spray 20 mg dose having essential the same AUC as the 25 mg reference tablet.

Tables 2, 3, and 4 summarize the statistical results of the analyses performed on the partial AUC intervals for non-dose adjusted sildenafil.

TABLE 2

Summary of Statistical Analysis Partial AUC Non-Dose Adjusted Test Product A
(1 Spray; 10 mg) vs. Reference Product (25 mg)
Test Product A (1 Spray; 10 mg) vs. Reference Product D
Geometric Means, Ratio of Means, and 90% Confidence Intervals Ln-Transformed Data
Sildenafil (Non-Dose Adjusted)
N = 24

| Parameter | Test A | Reference D | % Ratio | 90% CI |
|---|---|---|---|---|
| $AUC_{0-t}$ (ng-hr/mL) | 12.26 | 33.54 | 36.56 | (25.72, 51.97) |
| $AUC_{0-4}$ (ng-hr/mL) | 87.88 | 194.76 | 45.12 | (40.99, 49.68) |
| $AUC_{0-12}$ (ng-hr/mL) | 120.34 | 262.60 | 45.83 | (42.10, 49.88) |
| $AUC_{0-24}$ (ng-hr/mL) | ** | ** | ** | ** |

** Not calculated due to BLQ at the 24 hour time point
Source: Tables 1.2.1

TABLE 3

Summary of Statistical Analysis Partial AUC Non-Dose Adjusted Test Product B
(2 Spray; 20 mg) vs. Reference Product (25 mg)
Test Product B (2 Spray; 20 mg) vs. Reference Product D
Geometric Means, Ratio of Means, and 90% Confidence Intervals Ln-Transformed Data
Sildenafil (Non-Dose Adjusted)
N = 23

| Parameter | Test B | Reference D | % Ratio | 90% CI |
|---|---|---|---|---|
| $AUC_{0-1}$ (ng-hr/mL) | 28.75 | 32.09 | 89.58 | (63.07, 127.25) |
| $AUC_{0-4}$ (ng-hr/mL) | 186.46 | 195.08 | 95.58 | (86.76, 105.31) |
| $AUC_{0-12}$ (ng-hr/mL) | 255.44 | 263.26 | 97.03 | (89.08, 105.69) |
| $AUC_{0-24}$ (ng-hr/mL) | ** | ** | ** | ** |

** Not calculated due to BLQ at the 24 hour time point
Source: Tables 1.2.2

TABLE 4

Summary of Statistical Analysis Partial AUC Non-Dose Adjusted Test Product C
(3 Spray; 30 mg) vs. Reference Product (25 mg)
Test Product C (3 Spray; 30 mg) vs. Reference Product D
Geometric Means, Ratio of Means, and 90% Confidence Intervals La-Transformed Data
Sildenafil (Non-Dose Adjusted)
N = 24

| Parameter | Test C | Reference D | % Ratio | 90% CI |
|---|---|---|---|---|
| $AUC_{0-1}$ (ng-hr/mL) | 39.05 | 33.54 | 116.44 | (81.91, 165.51) |
| $AUC_{0-4}$ (ng-hr/mL) | 260.69 | 194.76 | 133.85 | (121.59, 147.36) |
| $AUC_{0-12}$ (ng-hr/mL) | 358.71 | 262.60 | 136.60 | (125.49, 148.70) |
| $AUC_{0-24}$ (ng-hr/mL) | ** | ** | ** | ** |

** Not calculated due to BLQ at the 24 hour time point
Source: Tables 1.2.3

When PK parameters $AUC_{0-1}$, $AUC_{0-4}$, $AUC_{0-12}$ for oral spray products Test A (10 mg), Test B (20 mg), and Test C (30 mg) were not dose-adjusted to the Reference D tablet (25 mg), statistical results for partial extent of sildenafil exposure from 0 to 1, 4, 12 and 24 hours in the test oral spray products as compared to the reference tablet product demonstrated that:
- there was a significant difference for partial $AUC_{0-1}$, $AUC_{0-4}$, $AUC_{0-12}$ for nondose adjusted Test product A (1 oral spray, 10 mg dose) of sildenafil as compared to the 25 mg tablet Reference D product. The extent of sildenafil exposure as calculated to one hour ($AUC_{0-1}$) was approximately 63% lower while AUC calculated to 4 and 12 hours were approximately 55% lower, respectively, than the Tablet Reference product consistent with the dose difference. (Refer to Table 2).
- the extent of exposure as calculated to 4 and 12 hrs (for non-dose adjusted $AUC_{0-4}$, $AUC_{0-12}$) Test product B (2 oral sprays, 20 mg dose) were comparable to the 25 mg tablet Reference D product as these values were within the 90% CI. However, partial AUC calculated to 1 hr was not contained within the 90% CI, although the point estimate was only slightly lower at approximately 10%. (As presented in Table 3).
- for Test Product C, 30 mg oral spray product, the non-dose adjusted partial $AUC_{0-1}$, $AUC_{0-4}$, $AUC_{0-12}$ of sildenafil was in general, reflective of the difference in dose from the 25 mg tablet Reference product (approximately 16, 34 and 37% higher, respectively) and all the values calculated for partial AUC from 0 to 1, 4 and 12 hrs were not within the 90% CI (Refer to Table 4).

Sildenafil (Dose Adjusted)

Table 5 presents a summary of the dose adjusted sildenafil pharmacokinetic parameters for each product using noncompartmental analysis.

TABLE 5

Summary Statistics and Partial AUC Values for Dose-Adjusted to 25 mg Sildenafil

| | Arithmetic Mean (% CV) | | | |
|---|---|---|---|---|
| Parameter | Test Product A (1 Spray; 10 mg) | Test Product B (2 Spray; 20 mg) | Test Product C (3 Spray; 30 mg) | Reference Product D (25 mg) |
| $AUC_{0-1}$ (ng · hr/mL) | 36.38 (59.09) | 47.50 (70.53) | 43.45 (68.57) | 51.89 (78.06) |
| $AUC_{0-4}$ (ng · hr/mL) | 247.84 (66.54) | 240.57 (42.74) | 232.56 (37.77) | 214.41 (48.29) |
| $AUC_{0-12}$ (ng · hr/mL) | 342.86 (68.42) | 328.57 (42.35) | 319.82 (38.10) | 288.63 (47.65) |
| $AUC_{0-24}$ (ng · hr/mL) |  () | 838.63 (***) | 551.41 (12.16) | 516.90 (46.74) |

** Not calculated due to BLQ at the 24 hour time point
Source: Tables 2.1.1-2.1.4

Statistical results presented in Table 5 for dose-adjusted partial PK parameters $AUC_{0-1}$, $AUC_{0-4}$, $AUC_{0-12}$ and $AUC_{0-24}$ demonstrates that:

- the dose adjusted $AUC_{0-4}$ for the sildenafil oral spray 10, 20 and 30 mg were in general comparable to the 25 mg Reference Tablet Sildenafil
- in general partial AUC calculated from 0 to 12 hrs for all 3 oral spray Test products of sildenafil was slightly higher than the 25 mg Reference tablet product (by approximately 11 to 19%. respectively).
- these results indicate that the partial extent of sildenafil exposure calculated for the first hour ($AUC_{0-1}$) were lower and for the next 4 hours ($AUC_{0-4}$) comparable but then higher when calculated to 12 hrs ($AUC_{0-12}$) for all the oral spray Test products as compared to the oral tablet Reference product.

Tables, 6, 7 and 8 summarize the results of the analyses performed on the pharmacokinetic parameters for dose adjusted sildenafil.

TABLE 6

Summary of Statistical Analysis Partial AUC Dose Adjusted Test Product A
(1 Spray; 10 mg) vs. Reference Product (25 mg)
Test Product A (1 Spray; 10 mg) vs. Reference Product D
Geometric Means, Ratio of Means, and 90% Confidence Intervals
Ln-Transformed Data
Sildenafil (Dose Adjusted)
N = 24

| Parameter | Test A | Reference D | % Ratio | 90% CI |
|---|---|---|---|---|
| $AUC_{0-1}$ (ng-hr/mL) | 30.65 | 33.54 | 91.40 | (64.30, 129.92) |
| $AUC_{0-4}$ (ng-hr/mL) | 219.70 | 194.76 | 112.81 | (102.47, 124.19) |
| $AUC_{0-12}$ (ng-hr/mL) | 300.85 | 262.60 | 114.57 | (105.25, 124.71) |
| $AUC_{0-24}$ (ng-hr/mL) | ** | ** | ** | ** |

** Not calculated due to BLQ at the 24 hour time point
Source: Tables 2.2.1

TABLE 7

Summary of Statistical Analysis Partial AUC Dose Adjusted Test Product B
(2 Spray; 20 mg) vs. Reference Product (25 mg)
Test Product B (2 Spray; 20 mg) vs. Reference Product D
Geometric Means, Ratio of Means, and 90% Confidence Intervals
Ln-Transformed Data
Sildenafil (Dose Adjusted)
N = 23

| Parameter | Test B | Reference D | % Ratio | 90% CI |
|---|---|---|---|---|
| $AUC_{0-1}$ (ng-hr/mL) | 35.93 | 32.09 | 111.98 | (78.84, 159.06) |
| $AUC_{0-4}$ (ng-hr/mL) | 233.08 | 195.08 | 119.48 | (108.45, 131.63) |
| $AUC_{0-12}$ (ng-hr/mL) | 319.29 | 263.26 | 121.28 | (111.35, 132.11) |
| $AUC_{0-24}$ (ng-hr/mL) | ** | ** | ** | ** |

** Not calculated due to BLQ at the 24 hour time point
Source: Tables 2.2.2

TABLE 8

Summary of Statistical Analysis Partial AUC Dose Adjusted Test Product C
(3 Spray; 30 mg) vs. Reference Product (25 mg)
Test Product C (3 Spray; 30 mg) vs. Reference Product D
Geometric Means, Ratio of Means, and 90% Confidence Intervals
Ln-Transformed Data
Sildenafil (Dose Adjusted)
N = 24

| Parameter | Test C | Reference D | % Ratio | 90% CI |
|---|---|---|---|---|
| $AUC_{0-1}$ (ng-hr/mL) | 32.54 | 33.54 | 97.03 | (68.26, 137.92) |
| $AUC_{0-4}$ (ng-hr/mL) | 217.24 | 194.76 | 111.54 | (101.32, 122.80) |
| $AUC_{0-12}$ (ng-hr/mL) | 298.93 | 262.60 | 113.83 | (104.57, 123.91) |
| $AUC_{0-24}$ (ng-hr/mL) | ** | ** | ** | ** |

** Not calculated due to BLQ at the 24 hour time point

When PK parameters partial $AUC_{0-1}$, $AUC_{0-4}$, and $AUC_{0-12}$ for sildenafil were dose adjusted to the 25 mg Reference Tablet formulation the partial systemic exposure of sildenafil in the oral spray products as compared to the Reference 25 mg tablet formulation demonstrated that (refer to Tables 6 to 8):

- the values of dose adjusted AUC calculated from 0 to 4 and to 12 hours of sildenafil for the 10 mg and 30 mg oral spray products were in general, comparable to the 25 mg tablet Reference product and were within the 90% CI., The 20 mg Test product B which was slightly higher compared to the 25 mg tablet Reference product and was not within the 90% CI.
- the values obtained for partial AUC calculated from 0 to 1 hr were, in general, not within the 90% CI indicating that partial extent of sildenafil exposure calculated to 1 hour for all oral spray Test products were not comparable to the 25 mg tablet Reference product.
- as the % Test/Reference point estimates indicate, the partial systemic sildenafil exposure at $AUC_{0-1}$, $AUC_{0-4}$, and $AUC_{0-12}$ for the 20 mg oral spray (Test Product B) was slightly more systemically bioavailable than the oral 25 mg reference tablet (112% vs 119.5% vs 121.3%, respectively).

N-desmethylsildenafil Partial AUC (Non-Dose Adjusted)

Table 9 presents a summary of the N-desmethylsildenafil partial AUC for each product using noncompartmental analysis.

TABLE 9

Summary Statistics and Partial AUC Values
for Non-Dose Adjusted N-desmethylsildenafil

|  | Arithmetic Mean (% CV) | | | |
| --- | --- | --- | --- | --- |
| Parameter | Test Product A (1 Spray; 10 mg) | Test Product B (2 Spray; 20 mg) | Test Product C (3 Spray; 30 mg) | Reference Product D (25 mg) |
| $AUC_{0-1}$ (ng·hr/mL) | 2.80 (78.07) | 8.35 (67.48) | 11.85 (66.83) | 14.30 (63.65) |
| $AUC_{0-4}$ (ng·hr/mL) | 18.03 (39.47) | 39.94 (37.04) | 61.44 (36.28) | 51.27 (31.44) |
| $AUC_{0-12}$ (ng·hr/mL) | 30.43 (37.65) | 64.28 (35.26) | 100.62 (35.15) | 80.25 (30.02) |
| $AUC_{0-24}$ (ng·hr/mL) | (**) | 87.14 (28.07) | 67.21 (26.25) | 69.32 (32.30) |

(**) Not calculated due to BLQ at the 24 hour time point
Source: Tables 3.1.1-3.1.4

Statistical results as presented in Table 9 for non-dose adjusted partial AUC parameters $AUC_{0-1}$, $AUC_{0-4}$, $AUC_{0-12}$ and $AUC_{0-24}$ of the metabolite N-desmethylsildenafil, demonstrates that:

- in general, for all doses of the sildenafil oral spray product, the extent of N-desmethylsildenafil exposure as assessed by partial AUC calculated from 0 to 4 and 12 hours, increased proportionally with increasing doses from 10 to 30 mg.
- in general the differences found between the N-desmethylsildenafil partial AUC were consistent with the dose difference of the oral spray and 25 mg reference tablet.

Tables 10, 11, and 12 summarize the results of the analyses performed on the partial AUC parameters for non-dose adjusted N-desmethylsildenafil.

TABLE 10

Summary of Statistical Analysis Partial AUC Non-Dose Adjusted Test Product
(1 Spray; 10 mg) vs. Reference Product (25 mg)
Test Product A (1 Spray; 10 mg) vs. Reference Product D
Geometric Means, Ratio of Means, and 90% Confidence Intervals
Ln-Transformed Data
N-desmethylsildenafil (Non-Dose Adjusted)
N = 24

| Parameter | Test A | Reference D | % Ratio | 90% CI |
| --- | --- | --- | --- | --- |
| $AUC_{0-1}$ (ng-hr/mL) | 1.83 | 10.54 | 17.40 | (10.78, 28.11) |
| $AUC_{0-4}$ (ng-hr/mL) | 16.88 | 48.57 | 34.76 | (32.25, 37.47) |
| $AUC_{0-12}$ (ng-hr/mL) | 28.38 | 76.21 | 37.24 | (34.82, 39.83) |
| $AUC_{0-24}$ (ng-hr/mL) | ** | ** | ** | ** |

** Not calculated due to BLQ at the 24 hour time point
Source: Tables 3.2.1

TABLE 11

Summary of Statistical Analysis Partial AUC Non-Dose Adjusted Test Product
(2 Spray; 20 mg) vs. Reference Product (25 mg)
Test Product B (2 Spray; 20 mg) vs. Reference Product D
Geometric Means, Ratio of Means, and 90% Confidence Intervals
Ln-Transformed Data
N-desmethylsildenafil (Non-Dose Adjusted)
N = 23

| Parameter | Test B | Reference D | % Ratio | 90% CI |
| --- | --- | --- | --- | --- |
| $AUC_{0-1}$ (ng-hr/mL) | 5.05 | 10.09 | 50.00 | (30.92, 80.87) |
| $AUC_{0-4}$ (ng-hr/mL) | 37.66 | 48.75 | 77.27 | (71.65, 83.32) |
| $AUC_{0-12}$ (ng-hr/mL) | 61.21 | 76.65 | 79.86 | (74.65, 85.44) |
| $AUC_{0-24}$ (ng-hr/mL) | 70.10 | 86.34 | 81.19 | (66.31, 99.40) |

Source: Tables 3.2.2

TABLE 12

Summary of Statistical Analysis Partial AUC Non-Dose Adjusted Test Product
(3 Spray; 30 mg) vs. Reference Product (25 mg)
Test Product C (3 Spray; 30 mg) vs. Reference Product D
Geometric Means, Ratio of Means, and 90% Confidence Intervals
Ln-Transformed Data
N-desmethylsildenafil (Non-Dose Adjusted)
N = 24

| Parameter | Test C | Reference D | % Ratio | 90% CI |
| --- | --- | --- | --- | --- |
| $AUC_{0-1}$ (ng-hr/mL) | 8.20 | 10.54 | 77.79 | (48.16, 125.63) |
| $AUC_{0-4}$ (ng-hr/mL) | 57.64 | 48.57 | 118.67 | (110.1, 127.91) |
| $AUC_{0-12}$ (ng-hr/mL) | 94.51 | 76.21 | 124.01 | (115.94, 132.63) |
| $AUC_{0-24}$ (ng-hr/mL) | 106.35 | 85.41 | 124.52 | (101.71, 152.46) |

Source: Tables 3.2.3

The non-dose adjusted to the 25 mg reference tablet N-desmethylsildenafil partial $AUC_{0-1}$, $AUC_{0-4}$, $AUC_{0-12}$ and $AUC_{0-24}$ of the oral spray doses as compared to the Reference 25 mg tablet formulation demonstrated that:

- the point estimates for non-dose adjusted partial AUC as calculated from 0 to 1 hour ($AUC_{0-1}$) of N-desmethylsildenafil for the 10, 20 and 30 mg oral spray doses were in general, lower to the difference in doses to the 25 mg tablet reference tablet
- the point estimates for partial AUC as calculated to 4, 12 and 24 hours for the 10 mg and 20 mg oral spray doses were generally consistent with the difference in mg dose to the 25 mg oral tablet N-desmethylsildenafil Partial AUC (Dose Adjusted)

Table 13 presents a summary of the dose adjusted N-desmethylsildenafil pharmacokinetic parameters for each product using noncompartmental analysis.

TABLE 13

Summary Statistics and Partial AUC Values for
Dose-Adjusted to 25 mg N-desmethylsildenafil

|  | Arithmetic Mean (% CV) | | | |
| --- | --- | --- | --- | --- |
| Parameter | Test Product A (1 Spray; 10 mg) | Test Product B (2 Spray; 20 mg) | Test Product C (3 Spray; 30 mg) | Reference Product D (25 mg) |
| $AUC_{0-1}$ (ng·hr/mL) | 6.99 (78.07) | 10.44 (67.48) | 9.87 (66.83) | 14.30 (63.65) |
| $AUC_{0-4}$ (ng·hr/mL) | 45.09 (39.47) | 49.93 (37.04) | 51.20 (36.28) | 51.27 (31.44) |
| $AUC_{0-12}$ (ng·hr/mL) | 76.07 (37.65) | 80.35 (35.26) | 83.85 (35.15) | 80.25 (30.02) |

TABLE 13-continued

Summary Statistics and Partial AUC Values for
Dose- Adjusted to 25 mg N-desmethylsildenafil

| | Arithmetic Mean (% CV) | | | |
|---|---|---|---|---|
| Parameter | Test Product A (1 Spray; 10 mg) | Test Product B (2 Spray; 20 mg) | Test Product C (3 Spray; 30 mg) | Reference Product D (25 mg) |
| $AUC_{0-24}$ (ng · hr/mL) | (**) | 108.93 (28.07) | 56.01 (26.25) | 69.32 (32.30) |

(**) Not calculated due to BLQ at the 24 hour time point
Source: Tables 4.1.1-4.1.4

After dose adjusting the partial $AUC_{0-1}$ for the 10, 20 and 30 mg oral spray doses, were found to be less than the 25 mg oral tablet dose.

The dose-adjusted AUCs calculated from 0 to 4 and 12 hours for the metabolite of Test products A, B and C were in general, comparable while no specific trend was observed for $AUC_{0-24}$ for all the oral spray Test products to the Reference Tablet product.

Tables 14, 15, 16 summarize the results of the analyses performed on the partial AUC for dose adjusted N-desmethylsildenafil.

TABLE 14

Summary of Statistical Analysis Partial AUC Dose Adjusted Test
Product A
(1 Spray; 10 mg) vs. Reference Product (25 mg)
Test Product A (1 Spray; 10 mg) vs. Reference Product D
Geometric Means, Ratio of Means, and 90% Confidence Intervals
Ln-Transformed Data
N-desmethylsildenafil (Dose Adjusted)
N = 24

| Parameter | Test A | Reference D | % Ratio | 90% CI |
|---|---|---|---|---|
| $AUC_{0-1}$ (ng-hr/mL) | 4.58 | 10.54 | 43.51 | (26.94, 70.28) |
| $AUC_{0-4}$ (ng-hr/mL) | 42.21 | 48.57 | 86.90 | (80.62, 93.66) |
| $AUC_{0-12}$ (ng-hr/mL) | 70.95 | 76.21 | 93.10 | (87.04, 99.57) |
| $AUC_{0-24}$ (ng-hr/mL) | ** | ** | ** | ** |

** Not calculated due to BLQ at the 24 hour time point
Source: Tables 4.2.1

TABLE 15

Summary of Statistical Analysis Partial AUC Dose Adjusted Test
Product B
(2 Spray; 20 mg) vs. Reference Product (25 mg)
Test Product B (2 Spray; 20 mg) vs. Reference Product D
Geometric Means, Ratio of Means, and 90% Confidence Intervals
Ln-Transformed Data
N-desmethylsildenafil (Dose Adjusted)
N = 23

| Parameter | Test B | Reference D | % Ratio | 90% CI |
|---|---|---|---|---|
| $AUC_{0-1}$ (ng-hr/mL) | 6.31 | 10.09 | 62.51 | (38.65, 101.09) |
| $AUC_{0-4}$ (ng-hr/mL) | 47.08 | 48.75 | 96.58 | (89.56, 104.15) |
| $AUC_{0-12}$ (ng-hr/mL) | 76.51 | 76.65 | 99.83 | (93.31, 106.80) |
| $AUC_{0-24}$ (ng-hr/mL) | 87.62 | 86.34 | 101.48 | (82.89, 124.25) |

Source: Tables 4.2.2

TABLE 16

Summary of Statistical Analysis Partial AUC Dose Adjusted Test
Product C
(3 Spray; 30 mg) vs. Reference Product (25 mg)
Test Product C (3 Spray; 30 mg) vs. Reference Product D
Geometric Means, Ratio of Means, and 90% Confidence Intervals
Ln-Transformed Data
N-desmethylsildenafil (Dose Adjusted)
N = 24

| Parameter | Test C | Reference D | % Ratio | 90% CI |
|---|---|---|---|---|
| $AUC_{0-1}$ (ng-hr/mL) | 6.83 | 10.54 | 64.82 | (40.13, 104.69) |
| $AUC_{0-4}$ (ng-hr/mL) | 48.03 | 48.57 | 98.89 | (91.75, 106.59) |
| $AUC_{0-12}$ (ng-hr/mL) | 78.76 | 76.21 | 103.34 | (96.62, 110.53) |
| $AUC_{0-24}$ (ng-hr/mL) | 88.63 | 85.41 | 103.77 | (84.75, 127.05) |

Source: Tables 4.2.3

When comparing the dose adjusted partial $AUC_{0-1}$, $AUC_{0-4}$, $AUC_{0-12}$ and $AUC_{0-24}$ N-desmethylsildenafil for the oral spray doses, the pharmacokinetic and statistical results for the N-desmethylsildenafil demonstrated that:

for the 1 spray (10 mg dose), 2 spray (20 mg dose) and 3 spray (30 mg dose) the AUC values of the metabolite as calculated to 4 and 12 hours were in general, all within the 90% CI criteria of 80-125% and therefore considered comparable to the 25 mg tablet Reference product.

the values obtained for partial AUC calculated to the first hour demonstrated that, in general for all oral spray Test products, values for $AUC_{0-1}$ were substantially lower than the tablet Reference product.

Metabolite/Parent Ratio Partial AUC (N-desmethylsildenafil/Sildenafil Ratio)

Table 17 presents a summary of the Metabolite/Parent Ratio (N-desmethylsildenafil/Sildenafil) pharmacokinetic parameters for each product.

TABLE 17

Summary Statistics and Partial AUC Values for Metabolite/Parent
Ratio (N-desmethylsildenafil/Sildenafil)

| | Arithmetic Mean (% CV) | | | |
|---|---|---|---|---|
| Parameter | Test Product A (1 Spray; 10 mg) | Test Product B (2 Spray; 20 mg) | Test Product C (3 Spray; 30 mg) | Reference Product D (25 mg) |
| $AUC_{0-1}$ | 0.19 (70.09) | 0.22 (52.90) | 0.24 (46.41) | 0.36 (56.31) |
| $AUC_{0-4}$ | 0.21 (43.62) | 0.22 (37.91) | 0.24 (36.00) | 0.28 (45.49) |
| $AUC_{0-12}$ | 0.26 (40.54) | 0.27 (37.03) | 0.28 (34.57) | 0.32 (44.25) |
| $AUC_{0-24}$ | ** (**) | ** (**) | ** (**) | ** (**) |

** Not calculated due to BLQ at the 24 hour time point
Source: Tables 5.1.1-5.1.4

Tables 18, 19, and 20 summarize the results of the analyses performed on the pharmacokinetic parameters for N-desmethyl sildenafil/Sildenafil Ratio.

TABLE 18

Summary of Statistical Analysis Partial AUC M/P Ratio Test Product
(1 Spray; 10 mg) vs. Reference Product (25 mg)
Test Product A (1 Spray; 10 mg) vs. Reference Product D
Geometric Means, Ratio of Means, and 90% Confidence Intervals
Ln-Transformed Data
N-desmethylsildenafil/Sildenafil Ratio
N = 24

| Parameter | Test A | Reference D | % Ratio | 90% CI |
|---|---|---|---|---|
| $AUC_{0-1}$ | 0.15 | 0.31 | 47.79 | (37.73, 60.52) |
| $AUC_{0-4}$ | 0.19 | 0.25 | 77.29 | (72.37, 82.54) |
| $AUC_{0-12}$ | 0.23 | 0.29 | 80.47 | (75.53, 85.72) |
| $AUC_{0-24}$ | ** | ** | ** | ** |

** Not calculated due to BLQ at the 24 hour time point
Source: Tables 5.2.1

TABLE 19

Summary of Statistical Analysis Partial AUC M/P Ratio Test Product
(2 Spray; 20 mg) vs. Reference Product (25 mg)
Test Product B (2 Spray; 20 mg) vs. Reference Product D
Geometric Means, Ratio of Means, and 90% Confidence Intervals
Ln-Transformed Data
N-desmethylsildenafil/Sildenafil Ratio
N = 23

| Parameter | Test A | Reference D | % Ratio | 90% CI |
|---|---|---|---|---|
| $AUC_{0-1}$ | 0.18 | 0.31 | 55.91 | (44.07, 70.94) |
| $AUC_{0-4}$ | 0.20 | 0.25 | 80.83 | (75.65, 86.37) |
| $AUC_{0-12}$ | 0.24 | 0.29 | 82.09 | (77.01, 87.49) |
| $AUC_{0-24}$ | ** | ** | ** | ** |

** Not calculated due to BLQ at the 24 hour time point
Source: Tables 5.2.2

TABLE 20

Summary of Statistical Analysis Partial AUC M/P Ratio Test Product
(3 Spray; 30 mg) vs. Reference Product (25 mg)
Test Product C (3 Spray; 30 mg) vs. Reference Product D
Geometric Means, Ratio of Means, and 90% Confidence Intervals
Ln-Transformed Data
N-desmethylsildenafil/Sildenafil Ratio
N = 24

| Parameter | Test A | Reference D | % Ratio | 90% CI |
|---|---|---|---|---|
| $AUC_{0-1}$ | 0.21 | 0.31 | 66.71 | (52.67, 84.48) |
| $AUC_{0-4}$ | 0.22 | 0.25 | 87.99 | (82.39, 93.97) |
| $AUC_{0-12}$ | 0.26 | 0.29 | 90.58 | (85.03, 96.49) |
| $AUC_{0-24}$ | ** | ** | ** | ** |

** Not calculated due to BLQ at the 24 hour time point
Source: Tables 5.2.3

Overall, the formation of the metabolite as assessed by the M/P ratio for the 10, 20 and 30 mg oral spray doses demonstrates that the most substantive difference was seen for AUC (0-1) interval. These differences were also essentially independent of the Test as dose (1 spray, 2 sprays and 3 sprays) as only minimal differences were seen between numbers of sprays. There was essentially no difference in partial AUC M/P ratio seen for the $AUC_{0-4}$ and $AUC_{0-12}$ hour intervals.

Discussion

The partial AUC assessment indicates that the most substantive difference between the sildenafil OS and the reference Viagra® tablet occurs at AUC (0-1) interval. There are then no substantive differences found in the partial AUC intervals 0-4, 0-12 and 0-24 between the test OS and the reference tablet. This was again demonstrated with the ratio of metabolite/parent where the most substantive difference is seen for AUC (0-1) interval. These differences were also essentially independent of the sildenafil OS dose (1 spray, 2 sprays and 3 sprays).

REFERENCES

Food and Drug Administration. Guidance for Industry: Bioavailability and Bioequivalence Studies for Orally Administered Drug Products—General Considerations. Center for Drug Evaluation and Research, March 2003.

Chow, S. C. and J. P. Liu. Design and Analysis of Bioavailability and Bioequivalence Studies, Second Edition, Revised and Expanded. New York: Marcel Dekker, Inc., 2000.

Pharsight Corporation. WinNonlin® User's Guide. Pharsight Corporation, 1998-2005.

SAS Institute, Inc. SAS OnlineDoc®, Version 9.1. Cary, N.C.: SAS Institute, Inc., 2002-2006.

Pharmacokinetics of sildenafil after single oral doses in healthy male subjects: absolute bioavailability, food effects and dose proportionality. Donald J. Nichols, Gary J. Muirhead, Jane A. Harness Br. J. Clin Pharmaco, Vol 53 supp. pages: 5S-12S, February 2002

Comparative human pharmacokinetics and metabolism of single-dose oral and intravenous sildenafil authors: Gary J. Muirhead, David J. Rance, Br. J. Clin Pharmaco, Vol 53 supp. Pages, 13S-20S, March 2002.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The terms "include," "includes," or "including" shall be deemed to be followed by the words "without limitation" unless otherwise indicated.

Each patent, patent application, and publication cited or described in the present application is hereby incorporated by reference in its entirety as if each individual patent, patent application, or publication was specifically and individually indicated to be incorporated by reference.

What is claimed is:

1. A method of treating pulmonary arterial hypertension and/or selective serotonin reuptake inhibitor (SSRI)-induced sexual dysfunction comprising administering to a subject in need thereof an oral spray formulation comprising a sildenafil base or a pharmaceutically acceptable salt thereof, wherein the pH of the formulation is 1.5 to 2.4.

2. The method of claim 1, wherein the sildenafil base or a pharmaceutically acceptable salt thereof is present in an amount of 6% to 14% w/v of the formulation.

3. The method of claim 2, wherein the sildenafil base is present in an amount of 8.31% w/v of the formulation.

4. The method of claim 1, wherein the sildenafil salt is present in an amount of 10% to 12% w/v of the formulation.

5. The method of claim 4, wherein the sildenafil salt is present in an amount of 11.67% w/v of the formulation.

6. The method of claim 4, wherein the sildenafil salt is sildenafil citrate.

7. The method of claim 1, wherein the formulation further comprises a polar solvent.

8. The method of claim 7, wherein the polar solvent comprises propylene glycol and ethyl alcohol.

9. The method of claim 8, wherein the ratio of propylene glycol:ethyl alcohol is 70:30% v/v, 65:35% v/v, 62.5:37.5% v/v, 60:40% v/v, 55:45% v/v or 50:50 v/v.

10. The method of claim 1, wherein the formulation further comprises a pH-adjusting agent, wherein the pH-adjusting agent is an acidifying agent, an alkalizing agent, or a combination thereof.

11. The method of claim 10, wherein the acidifying agent is hydrochloric acid (HCl).

12. The method of claim 10, wherein the alkalizing agent is sodium hydroxide (NaOH).

13. The method of claim 1, wherein the formulation further comprises a taste-masking agent, a flavoring agent, or a combination thereof.

14. The method of claim 13, wherein the taste-masking agent or the flavoring agent is a sweetener.

15. The method of claim 13, wherein the taste-masking agent or the flavoring agent is a fruit flavor, a chocolate flavor, or a combination thereof.

16. The method of claim 14, wherein the sweetener is sucralose.

17. The method of claim 1, wherein the formulation further comprises a pharmaceutically acceptable excipient, a carrier, or a combination thereof.

18. The method of claim 1, wherein the amount of sildenafil administered per spray is between about 10 mg and about 30 mg.

19. The method of claim 1, wherein the pH of the formulation is 1.5, 1.6, 1.7, 1.8, 1.9, 2.0, 2.1, 2.2, 2.3, or 2.4.

\* \* \* \* \*